(12) United States Patent
Lin

(10) Patent No.: US 12,281,291 B1
(45) Date of Patent: Apr. 22, 2025

(54) MINIATURIZED COMPARTMENT SYSTEM FOR IN-VITRO FERTILIZATION (IVF)

(71) Applicant: IVFpro LLC, Pittsburgh, PA (US)

(72) Inventor: Ta-Chin Lin, Tainan (TW)

(73) Assignee: IVFpro LLC, Pittsburgh, PA (US)

( * ) Notice: Subject to any disclaimer, the term of this patent is extended or adjusted under 35 U.S.C. 154(b) by 0 days.

(21) Appl. No.: 18/888,633

(22) Filed: Sep. 18, 2024

Related U.S. Application Data

(60) Provisional application No. 63/660,263, filed on Jun. 14, 2024.

(51) Int. Cl.
| | |
|---|---|
| *C12M 3/00* | (2006.01) |
| *C12M 1/00* | (2006.01) |
| *C12M 1/12* | (2006.01) |
| *C12M 1/34* | (2006.01) |
| *C12M 1/36* | (2006.01) |
| *A61B 17/43* | (2006.01) |
| *A61B 17/435* | (2006.01) |

(52) U.S. Cl.
CPC ............ *C12M 21/06* (2013.01); *C12M 23/58* (2013.01); *C12M 37/02* (2013.01); *C12M 41/12* (2013.01); *C12M 41/34* (2013.01); *C12M 41/48* (2013.01); *A61B 17/43* (2013.01); *A61B 17/435* (2013.01)

(58) Field of Classification Search
CPC ...... C12M 41/14; C12M 41/00; C12M 41/48; C12M 41/36; C12M 41/34; C12M 41/26; C12M 41/12; C12M 41/06; C12M 23/48; C12M 23/58; C12M 33/00; C12M 21/06; B01L 7/52; B01L 7/00; B01L 23/0829; A61B 17/43; A61B 17/435
See application file for complete search history.

(56) References Cited

U.S. PATENT DOCUMENTS

2018/0079999 A1* 3/2018 Blanchard .............. C12M 23/16
2018/0087021 A1* 3/2018 Blanchard .......... G01N 35/0099

OTHER PUBLICATIONS

LabIVF® homepage, "IVF Chamber—IVFtech Unica Semi Closed IVF workstation", https://labivf.com/ivf-chamber/, retrieved Dec. 9, 2024, 4 pages.
Teck Event homepage, "Cell-Tek Microscope Chambers", https://web.archive.org/web/20230925091906/https:/tekevent.com/cell-tek-microscope-chambers/, retrieved Dec. 9, 2024, 4 pages.

* cited by examiner

*Primary Examiner* — Michael L Hobbs
(74) *Attorney, Agent, or Firm* — Knobbe Martens Olson & Bear LLP

(57) ABSTRACT

The present disclosure generally relates to miniaturized chambers for automatically conducting cell culture under controlled environment conditions. In some implementation examples, a system includes a first chamber, a second chamber, and a control subsystem. The control subsystem detects a first environment condition associated with the first chamber and a second environment condition associated with the second chamber. Based at least on the first environment condition and a first airflow mode, the control subsystem supplies a first airflow to the first chamber to adjust the first environment condition toward a first target environment condition. Based at least on the second environment condition and a second airflow mode, the control subsystem supplies a second airflow to the second chamber to adjust the second environment condition toward a second target environment condition.

32 Claims, 18 Drawing Sheets

MINIATURIZED COMPARTMENT SYSTEM FOR IN-VITRO FERTILIZATION (IVF)

CROSS-REFERENCE TO RELATED APPLICATIONS

This application claims priority to U.S. Provisional Patent Application No. 63/660,263 titled "MINIATURIZED AUTOMATIC INCUBATOR SYSTEM" and filed on Jun. 14, 2024, the disclosure of which is hereby incorporated by reference in its entirety and for all purposes.

FIELD OF THE DISCLOSURE

The present disclosure relates to devices for cell culture, and more particularly, to incubator systems that control environment conditions for cell culture.

BACKGROUND

In recent years, there have been advancements and applications related to cell culture which is a process for growing cells under controlled conditions. Cell culture vessels or modules that include cells are stored in incubators which maintain certain environment conditions suitable for cell growth. An example application of cell culture includes in vitro fertilization ("IVF").

However, cell culture, and applications thereof, suffer from technological problems. As an example, certain environment conditions may be critical to the success of cell culture. Indeed, environmental fluctuations may introduce cause negative effects. Additionally, at present cell culture requires laborious efforts from professionals or technicians. This high level of human involvement can cause environment conditions within incubators to change or deviate from favorable environment conditions.

SUMMARY

In some aspects, the techniques described herein relate to a system for cell culture within a case that structurally accommodates at least a first chamber, a second chamber, and at least a portion of an environment control subsystem, the system including: the first chamber configured to store a plurality of culture vessels including biological samples; the second chamber adjacent to the first chamber and fluidically isolated from the first chamber by first one or more movable structures based on the first one or more movable structures being in a closed configuration, wherein the second chamber is configured to accommodate at least a manipulator assembly for manipulating the plurality of culture vessels; and the environment control subsystem, wherein the environment control subsystem individually controls respective environments within the first chamber and the second chamber, and wherein the environment control subsystem is configured to: detect a first environment condition that specifies a current temperature of the first chamber, a current humidity of the first chamber, and a current air composition of the first chamber; detect a second environment condition that specifies a current temperature of the second chamber, a current humidity of the second chamber, and a current air composition of the second chamber; supply, via a first airflow mode determined based on a first cell culture activity conducted inside the first chamber, a first airflow to the first chamber to adjust the first environment condition toward a first target environment condition; and supply, via a second airflow mode determined based on a second cell culture activity conducted inside the second chamber, a second airflow to the second chamber to adjust the second environment condition toward a second target environment condition.

In some aspects, the techniques described herein relate to a system, wherein the environment control subsystem includes a housing that houses at least a portion of an air quality controller, wherein the housing is outside the case, and wherein the air quality controller is configured to supply the first airflow and the second airflow.

In some aspects, the techniques described herein relate to a system, wherein the air quality controller includes an air heater, a humidifier, a volatile organic compounds (VOC) filter, a high-efficiency particulate air (HEPA) filter, an oxygen absorber, and a carbon dioxide absorber.

In some aspects, the techniques described herein relate to a system, wherein the environment control subsystem includes a first airflow assembly and a second airflow assembly, and wherein: the first airflow assembly supplies the first airflow to the first chamber to adjust the first environment condition toward the first target environment condition; and the second airflow assembly supplies the second airflow to the second chamber to adjust the second environment condition toward the second target environment condition.

In some aspects, the techniques described herein relate to a system, wherein a first end of the first airflow assembly is inside the housing and a second end of the first airflow assembly is inside the first chamber, and wherein a first end of the second airflow assembly is inside the housing and a second end of the second airflow assembly is inside the second chamber.

In some aspects, the techniques described herein relate to a system, wherein the environment control subsystem includes a plurality of sensors configured to detect the first environment condition and the second environment condition, and wherein the plurality of sensors are housed in the housing and include a pressure sensor, a temperature sensor, a humidity sensor, and an air composition sensor.

In some aspects, the techniques described herein relate to a system, wherein when the first airflow mode is a one-way airflow mode, to supply the first airflow includes injecting air inlets from an air tank without circulating air inside the first chamber.

In some aspects, the techniques described herein relate to a system, wherein the environment control subsystem includes an air reservoir that is different from the air tank, and wherein the environment control subsystem is further configured to: determine that the current air composition of the first chamber deviates from an air composition specified by the first target environment condition above a predetermined threshold; and responsive to determining that the current air composition of the first chamber deviates from the air composition specified by the first target environment condition, cause the air reservoir to flush air to the first chamber to adjust the current air composition of the first chamber toward the air composition specified by the first target environment condition.

In some aspects, the techniques described herein relate to a system, wherein when the first airflow mode is a close airflow mode, to supply the first airflow includes circulating air inside the first chamber without injecting air inlets from an air tank.

In some aspects, the techniques described herein relate to a system, wherein when the first airflow mode is a semi-close airflow mode, to supply the first airflow includes circulating air inside the first chamber and injecting air inlets from an air tank according to a predetermined ratio.

In some aspects, the techniques described herein relate to a system, wherein the first airflow mode is a one-way airflow mode, and the second airflow mode is a semi-close airflow mode or a close airflow mode.

In some aspects, the techniques described herein relate to a system, wherein the first cell culture activity conducted inside the first chamber includes culturing unknown cells or cells that are toxic to an environment external to the case.

In some aspects, the techniques described herein relate to a system, wherein the environment control subsystem includes a first heater deployed inside the first chamber, and wherein the environment control subsystem is further configured to activate the first heater to adjust the current temperature of the first chamber toward a temperature specified by the first target environment condition.

In some aspects, the techniques described herein relate to a system, wherein the environment control subsystem includes a first air absorber deployed outside the first chamber, and wherein the environment control subsystem activates the first air absorber based on the first airflow mode to adjust the current air composition of the first chamber toward an air composition specified by the first target environment condition.

In some aspects, the techniques described herein relate to a system, wherein a temperature specified by the first target environment condition is between 36.5° C. (Celsius) to 37.5° C., a humidity specified by the first target environment condition is between 38% to 42%, and an air composition specified by the first target environment condition includes 5%-7% oxygen, 5%-10% carbon dioxide, and 88%-90% nitrogen.

In some aspects, the techniques described herein relate to a system, wherein a combined volume of the first chamber and the second chamber is less than 500 L.

In some aspects, the techniques described herein relate to a system, wherein to supply the first airflow includes filtering air inlets from an air tank and/or air inside the first chamber using a volatile organic compounds (VOC) filter and a high-efficiency particulate air (HEPA) filter.

In some aspects, the techniques described herein relate to a system, wherein the environment control subsystem is further configured to determine the first airflow mode based at least on a size of the first chamber or a remaining capacity of an air tank that supplies the first airflow.

In some aspects, the techniques described herein relate to a system, wherein the environment control subsystem is further configured to determine the second airflow mode based at least on a size of the second chamber or a remaining capacity of an air tank that supplies the second airflow.

In some aspects, the techniques described herein relate to a system, wherein the biological samples include one of oocytes, embryos, ovums, sperms, organoid, cells, or tissues.

In some aspects, the techniques described herein relate to a system, wherein: when the first airflow mode is a one-way airflow mode, the environment control subsystem is further configured to control a total air change per hour (TACH) associated with the first chamber without controlling a fresh air change per hour (FACH) associated with the first chamber; and when the first airflow mode is a semi-close airflow mode or a close airflow mode, the environment control subsystem is further configured to control the TACH associated with the first chamber and the FACH associated with the first chamber.

In some aspects, the techniques described herein relate to a system, wherein the environment control subsystem is further configured to adjust the first environment condition toward the first target environment condition using a ultra-violet (UV) light and/or radiant catalytic ionization (RCI).

In some aspects, the techniques described herein relate to a system, wherein the first target environment condition is the same as or different from the second target environment condition.

In some aspects, the techniques described herein relate to a system, further including an intelligent manipulator subsystem that includes the manipulator assembly, a camera assembly, a thermal camera, one or more processors and non-transitory computer storage media storing instructions, and an object temperature controller, wherein: the camera assembly is configured to generate image data; the thermal camera is configured to generate thermal imaging data; the one or more processors are configured to execute the instructions to generate, via a machine learning model based on the image data and the thermal imaging data, real-time information associated with one or more objects to be manipulated by the manipulator assembly; and the object temperature controller is configured to generate, based on the thermal imaging data and the real-time information, one or more thermal control signals, wherein the environment control subsystem supplies the first airflow and the second airflow further based on the one or more thermal control signals.

In some aspects, the techniques described herein relate to a system, wherein the environment control subsystem supplies the first airflow and the second airflow further based on the one or more thermal control signals.

In some aspects, the techniques described herein relate to a system, wherein the camera assembly includes a visual camera, a microscopic camera, and a microscopic front camera.

In some aspects, the techniques described herein relate to a system, wherein the visual camera and the thermal camera are installed at a ceiling of the second chamber, and wherein the microscopic camera and the microscopic front camera are installed on the manipulator assembly.

In some aspects, the techniques described herein relate to a system, wherein the machine learning model is configured to: extract features associated with the one or more objects based on the image data and/or the thermal imaging data, and generate the real-time information based on the features.

In some aspects, the techniques described herein relate to a system, wherein the machine learning model is one of a support vector machine (SVM), a deep learning model, or a neural network.

In some aspects, the techniques described herein relate to a system, further including a third chamber configured to conduct a cryopreservation procedure or a thawing procedure, wherein the third chamber is adjacent to the second chamber and fluidically isolated from the second chamber by second one or more movable structures based on the second one or more movable structures being in the closed configuration, and wherein the environment control subsystem is further configured to: detect a third environment condition that specifies a current temperature of the third chamber, a current humidity of the third chamber, and a current air composition of the third chamber; and supply, via a third airflow mode determined based on a third cell culture activity conducted inside the third chamber, a third airflow to the third chamber to adjust the third environment condition toward a third target environment condition.

In some aspects, the techniques described herein relate to a method implemented by a miniaturized system for cell culture, wherein the miniaturized system includes a first chamber configured to store a plurality of culture vessels including biological samples and a second chamber configured to accommodate at least a manipulator assembly for manipulating the plurality of culture vessels, the method including: detecting a first environment condition that specifies a current temperature of the first chamber, a current humidity of the first chamber, and a current air composition of the first chamber; detecting a second environment condition that specifies a current temperature of the second chamber, a current humidity of the second chamber, and a current air composition of the second chamber; supplying, via a first airflow mode determined based on a first cell culture activity conducted inside the first chamber, a first airflow to the first chamber to adjust the first environment condition toward a first target environment condition; and supplying, via a second airflow mode determined based on a second cell culture activity conducted inside the second chamber, a second airflow to the second chamber to adjust the second environment condition toward a second target environment condition.

In some aspects, the techniques described herein relate to a method, wherein when the first airflow mode is a one-way airflow mode, supplying the first airflow includes injecting air inlets from an air tank without circulating air inside the first chamber.

In some aspects, the techniques described herein relate to a method, wherein when the first airflow mode is a close airflow mode, supplying the first airflow includes circulating air inside the first chamber without injecting air inlets from an air tank.

In some aspects, the techniques described herein relate to a method, wherein when the first airflow mode is a semi-close airflow mode, supplying the first airflow includes circulating air inside the first chamber and injecting air inlets from an air tank according to a predetermined ratio.

In some aspects, the techniques described herein relate to a method, wherein the first airflow mode is a one-way airflow mode, and the second airflow mode is a semi-close airflow mode or a close airflow mode.

In some aspects, the techniques described herein relate to a method, wherein the first target environment condition is the same as or different from the second target environment condition.

In some aspects, the techniques described herein relate to a method, wherein a temperature specified by the first target environment condition is between 36.5° C. (Celsius) to 37.5° C., a humidity specified by the first target environment condition is between 38% to 42%, and an air composition specified by the first target environment condition includes 5%-7% oxygen, 5%-10% carbon dioxide, and 88%-90% nitrogen.

In some aspects, the techniques described herein relate to a method, wherein a combined volume of the first chamber and the second chamber is less than 500 L.

In some aspects, the techniques described herein relate to a method, wherein supplying the first airflow includes filtering air inlets from an air tank and/or air inside the first chamber using a volatile organic compounds (VOC) filter and a high-efficiency particulate air (HEPA) filter.

In some aspects, the techniques described herein relate to a method, wherein the biological samples include one of oocytes, embryos, ovums, sperms, organoid, cells, or tissues.

In some aspects, the techniques described herein relate to a system for cell culture within a case that structurally accommodates at least a first chamber, a second chamber, and at least a portion of an environment control subsystem, the system including: the first chamber configured to store a plurality of culture vessels including biological samples; the second chamber adjacent to the first chamber and fluidically isolated from the first chamber by first one or more movable structures based on the first one or more movable structures being in a closed configuration, wherein the second chamber is configured to accommodate at least a manipulator assembly for manipulating the plurality of culture vessels; and the environment control subsystem configured to: detect a first environment condition that specifies a current temperature of the first chamber, a current humidity of the first chamber, and a current air composition of the first chamber; detect a second environment condition that specifies a current temperature of the second chamber, a current humidity of the second chamber, and a current air composition of the second chamber; supply, via a first airflow mode, a first airflow to the first chamber to adjust the first environment condition toward a first target environment condition; and supply, via a second airflow mode, a second airflow to the second chamber to adjust the second environment condition toward a second target environment condition, wherein: when the first airflow mode is a one-way airflow mode, to supply the first airflow includes injecting air inlets from an air tank without circulating air inside the first chamber; when the first airflow mode is a close airflow mode, to supply the first airflow includes circulating the air inside the first chamber without injecting the air inlets from the air tank; and when the first airflow mode is a semi-close airflow mode, to supply the first airflow includes circulating the air inside the first chamber and injecting the air inlets from the air tank according to a predetermined ratio.

In some aspects, the techniques described herein relate to a system, wherein the environment control subsystem is further configured to: determine the first airflow mode based on a first cell culture activity conducted inside the first chamber; and determine the second airflow mode based on a second cell culture activity conducted inside the second chamber.

In some aspects, the techniques described herein relate to a system, wherein the first cell culture activity includes culturing unknown cells or cells that are toxic to an environment external to the case.

In some aspects, the techniques described herein relate to a system, wherein the second cell culture activity includes manipulating oocytes, embryos, ovums, or sperms.

DETAILED DESCRIPTION

Figure 1:
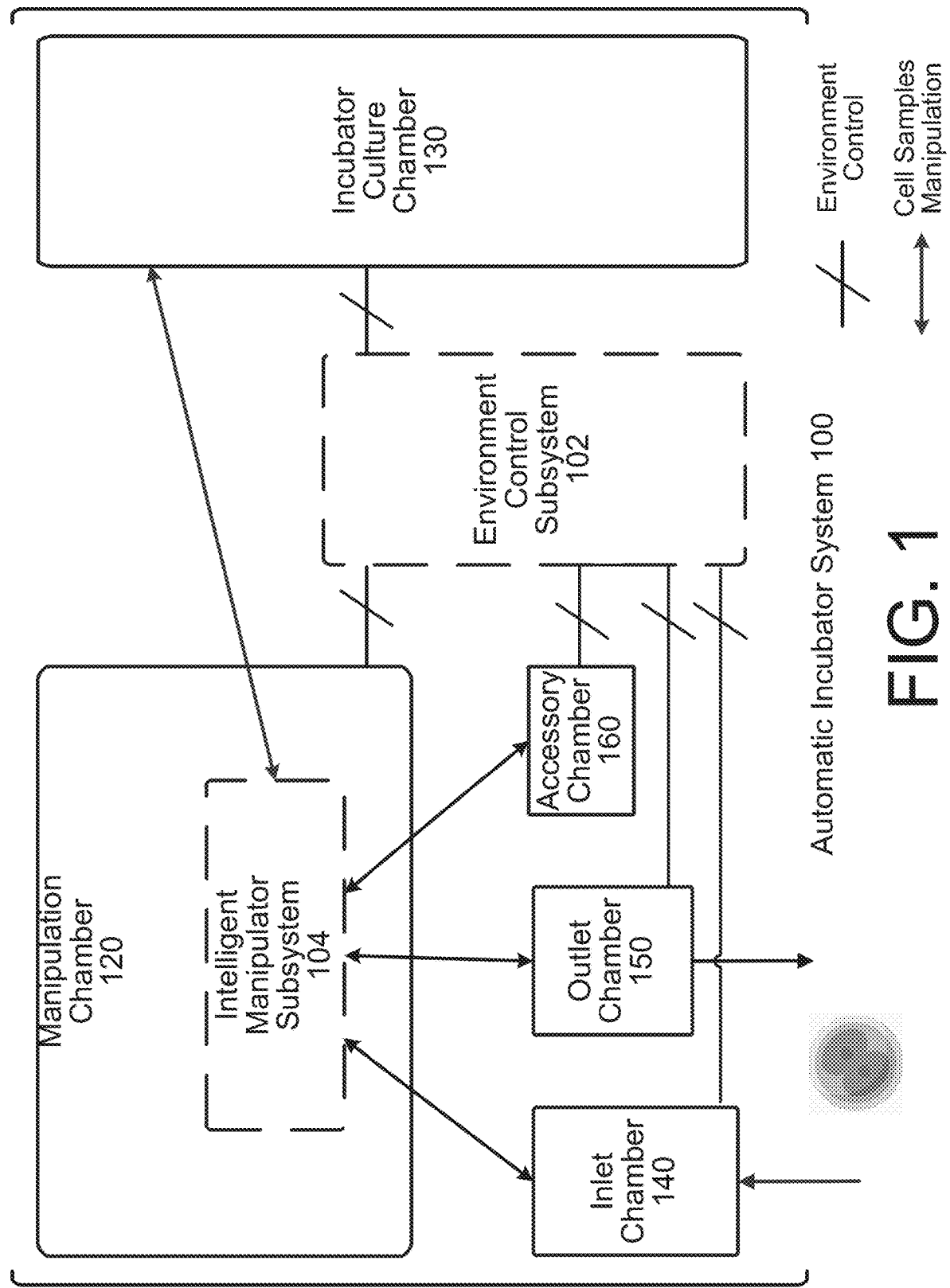
FIG. 1 is a block diagram of an example automatic incubator system which includes various chambers, an environment control subsystem, and an intelligent manipulator subsystem in accordance with some embodiments of the present disclosure.

This specification describes devices and techniques for controlling environment conditions (e.g., environmental conditions) for cell culture to increase success rate of cell culture, such as in vitro fertilization (IVF) cell culture. As will be described, a system may leverage various environment control mechanisms, sensing technologies and/or automation techniques to control and maintain environment conditions in one or more chambers of the system toward a target condition. The target condition may specify a particular combination of temperature, humidity, air pressure, and/or air composition. In some embodiments, the system may utilize airflow control mechanisms (e.g., flowing air to a chamber) in conjunction with non-airflow control mechanisms (e.g., heating a surface inside the chamber). For example, these mechanisms may be used to effectively maintain, or restore, environment conditions in the chamber(s) to a target condition within a threshold period of time. In this example, the environment conditions may be maintained in response to detecting environment condition fluctuations. Additionally, the system may apply distinct airflow control mechanisms (e.g., with or without circulating air) to various chambers associated with cell culture for controlling conditions in respective chambers.

In some embodiments, the system may utilize visual cameras, optionally in combination with thermal cameras, to perform automated actions on cells in culture vessels. For example, the system may control a manipulator assembly (e.g., a robotic arm) to manipulate the cells. With respect to thermal cameras, in some embodiments the system may use thermal imaging data to control the temperature at specific portions of the system. In contrast, prior techniques relied upon high level of manual labor for conducting cell culture without accurately maintaining environment conditions in chambers associated with cell culture, which may decrease chances of successful culture.

Typically, administering cell culture may involve human labor during progressions through various cultural stages. With respect to IVF, example stages may include oocyte recovery to insemination and culture of embryos. During these stages, human labor and manual operations are usually involved extensively. For example, embryologists operating a manipulation system may manipulate eggs, such as denuding oocytes for in clinical intracytoplasmic sperm injection (ICSI), stored in a culture incubator chamber. One major challenge to accomplish successful cell culture is accurately maintaining environment conditions within the culture incubator chamber, such as temperature and air composition suitable or optimized for culture. For example, the presence of embryologists or other personnel around a culture incubator chamber for administering IVF may cause environment conditions within the culture incubator chamber to fluctuate. As another example, transporting biological samples (e.g., oocytes, or embryos, or the like) from a culture incubator chamber to a working area for manipulation may cause environment conditions associated with the biological samples to fluctuate. In both examples, environment conditions may not be accurately maintained and may deviate from optimal environment conditions for cell culture.

More specifically, when an embryologist enters or leaves a working or manipulation area to operate a working station, temperature, humidity, and/or air composition within the culture incubator chamber may change due to differing environment conditions inside and outside the culture incubator chamber. As known by those skilled in the art, changes of environment conditions can negatively impact results of cell culture (e.g., impede healthy growth of an embryo). Although human presence can be limited (e.g., through shortening operation time of professionals in the vicinity of culture incubator chambers) to better control environment conditions, this may increase human errors due to increased stress resulted from operating under significantly constrained amount of time. Human errors may lead to reduced chances of successful cell culture or undesired consequences, such as harming viability of eggs. For example, undesired consequences may include decreased blastocyst formation, increased chromosome anomaly or fragmentation, decreased implantation rates, increased abnormal epigenetic patterns and abortion rates, and so on.

Additionally, even without the presence of, or intervention by, humans, environment conditions within a culture incubator chamber may still fluctuate. For example, environment conditions may change due to air consumed or released by cells during growth. Environment conditions may also change due to importing, exporting, or exchanging biological specimens between the culture incubator chamber and external area. As has been demonstrated, these changes of environment conditions within the culture incubator chamber may be detrimental to the success of cell culture. For example, when air composition changes (e.g., increased or decreased carbon dioxide level) due to cell growth, pH in a culture vessel may deviate from suitable levels for culturing cells, leading to unsatisfactory cell culture results.

Further, desired or optimized conditions for cell culture may vary during progressions through various stages of culture. For example, in the context of IVF treatment or IVM (in vitro maturation), desired percentage of oxygen in air surrounding an oocyte or an early embryo may differ as the oocyte matures or the embryo develops. More specifically, mean oxygen consumption by healthy looking oocytes may differ when measured after a culture period of three days compared with when measured after a culture period of eight days. For embryo development, different stages of embryos may have different oxygen consumptions because of different capacities associated with anaerobic and aerobic metabolisms. More specifically, mean oxygen consumed by two-cell embryos may change between during blastocyst and after a culture period of more than five days within human bodies. Further, mean oxygen consumption by non-human embryos may change even to greater extents compared with human embryos. As such, rigidly fixing environment conditions may yield inferior cell culture results.

To address at least a portion of the aforementioned problems, the system described herein (generally collectively referred to herein as "an automatic incubator system" or simply a "system") may use innovative automation technologies within a cohesive incubator unit or system. As will be described, environment control mechanisms (e.g., air quality and temperature control) may be used. In some embodiments, machine learning techniques may be used to accurately, and adaptively, control the environment conditions. The system may also automatically manipulate cell culture vessels which include biological samples (e.g., tissues, oocytes, embryos, or the like) without, or with limited, human labor.

The system may include miniaturized chambers within which environment conditions can be maintained at target conditions through both airflow control and non-airflow control mechanisms. In some embodiments, airflow control mechanisms may include at least controlling air quality toward a desired quality (e.g., desired temperature, humidity, pressure, and/or composition) through filtering circulated air. In other embodiments, airflow control mechanisms may include at least supplying air inlets (e.g., air that is stored in an air tank and has not been circulated) to a particular chamber using an airflow assembly (e.g., valves and tubes). Non-airflow control mechanisms may include use of heaters to heat certain surfaces within a chamber and/or using air absorbers to absorb excess amount of oxygen, carbon dioxide, nitride, or other composition of air in the chamber.

In some embodiments, the system may include a manipulation chamber, an incubator culture chamber, an inlet chamber, an outlet chamber, and an accessory chamber. The manipulation chamber may be utilized to accommodate components (e.g., robotic arms, visual cameras, or the like) for manipulating the biological samples. The incubator culture chamber may store cell culture vessels or modules that include the biological samples for cell growth. The inlet chamber may include one or more inlet rooms that may be utilized to receive the biological samples into the system, before transporting the biological samples to the manipulation chamber and/or the incubator culture chamber. The outlet chamber can be utilized to accommodate transport pods that include the biological samples for transporting to environment external to the system. The accessory chamber may be utilized for various purposes, such as cryopreservation. In some examples, the manipulation chamber, the incubator culture chamber, the inlet chamber, the outlet chamber, and the accessory chamber may be structurally (e.g., separated by walls, sliding doors, or the like) and/or fluidically (e.g., air from one chamber may not easily flow to another chamber) isolated from each other. As such, the system may have the flexibility to separately control environment conditions (e.g., based on particular cell culture activities or operations that are conducted in respective chambers) within individual chambers. Additionally, by deploying various chambers within an integral space (e.g., within a case) that provides isolation to external environments, the system can advantageously enable various cell culture related operations to all be conducted automatically within the case and avoid fluctuations of environment conditions during process and transportation of culture vessels. In some examples, the system may further include a housing outside the manipulation chamber, the incubator culture chamber, the inlet chamber, the outlet chamber, and the accessory chamber. The housing may house at least air quality control equipment (e.g., air absorbers, air filters, or the like) that can be utilized to manage environment conditions within each of the chambers.

Advantageously, through the coordination between airflow and non-airflow control mechanisms, the system may more effectively persist air quality within a threshold period of time (e.g., 1 second, 5 seconds, 10 seconds, and so on). Depending on types of applications and stages of cell culture, for example as determined by the system or as identified by a user, the system may adjust the target condition to provide improved environments for cell culture.

Additionally, the system may adopt distinct airflow control mechanisms for individual chambers. For example, the system may utilize one-way airflow mode to provide air to an incubator culture chamber. Under the one-way airflow mode, air in the incubator culture chamber may not be periodically circulated. Rather, the system may periodically supply air inlets stored in air tanks through air tubes into the incubator culture chamber while allowing previously supplied air to flow out of the incubator culture chamber. Concurrently, the system may utilize a semi-close, or close airflow, mode to provide air to any of the manipulation chamber, the incubator culture chamber, the inlet chamber, the outlet chamber, and the accessory chamber. For example, the system may utilize the semi-close, or close airflow, mode to provide air to the manipulation chamber in which a manipulator assembly may autonomously manipulate cells. In some embodiments, the manipulator assembly may obtain (e.g., grab or otherwise transfer) the cells from the culture chamber to the manipulation chamber. Under the close airflow mode, the system may circulate air in the manipulation chamber without injecting any air inlets. Under the semi-close airflow mode, the system may supplement air in the manipulation chamber with newly supplied air.

In some embodiments, the system may determine which of the airflow modes are suitable for individual chambers. For example, the system may select an airflow mode based on information including the sizes of chambers, types of cell culture which are being conducted, remaining air inlets capacity inside air tanks, or the like. The system may respond to environment condition changes differently or more appropriately depending on which airflow mode is selected. For example, and with respect to the one-way airflow mode, the system may detect that the oxygen level (e.g., 8%) in the air inside an incubator culture chamber is higher than a desired level (e.g., 5%). In this example, the system may inject air inlets that include a lesser percentage of oxygen. As another example, based on selection of the semi-close or close airflow mode, the system may trigger activation of an oxygen absorber to reduce oxygen in the air to adjust air composition within, for example, the incubator culture chamber.

In some embodiments, when changes of air composition exceed a particular degree, the system may resort to certain mechanisms that more quickly adjust air composition compared with circulating and filtering existing air. For example, when the nitrogen level increases by at least a threshold percentage (e.g., due to liquid nitrogen being in a chamber), the system may flush air stored in an air reservoir associated with the chamber to immediately flow into the chamber to reduce nitrogen level. Rather than circulating, filtering, and flowing air through an air tube, flushing air from the air reservoir into the chamber may advantageously enable the nitrogen level to be more quickly restored back to the desired level (e.g., 89%).

As described above, the airflow and non-airflow control mechanisms may leverage thermal imaging data. For example, when thermal imaging data indicates that the temperature of an object (e.g., liquid within a pipette) deviates from a desired temperature, the system may use an airflow control mechanism to cause warmer, or cooler, air to flow toward the object. As another example, when thermal imaging data indicates that the temperature inside an object (e.g., a Petri dish) deviates from a desired temperature, the system may use a non-airflow control mechanism to adjust its temperature. For this example, the system may activate a heater, or a cooling device, which is in proximity to the object. Advantageously, the thermal imaging data provides actionable insights into temperatures of arbitrary locations within the system.

The system may additionally control an included manipulator assembly to manipulate biological samples. More specifically, the system may control the manipulator assembly using machine learning techniques which analyze image data optionally in combination with the thermal imaging data. In this way, the system may obtain real-time information (e.g., identity, position, temperature, or the like) about objects which are to be manipulated, and manipulate the objects based on the real-time information. In some examples, the system may utilize computer vision techniques to process image data, and optionally thermal imaging data, to derive or extract features (e.g., shape features) associated with the objects. The extracted features of objects may then be used to train, or run inferences using, a machine learning model. The training process may include using at least a subset of the derived features to train the machine learning model. The trained machine learning model may then be employed to generate information about objects for generating motion control signals to control operations of the manipulator assembly to manipulate biological samples without human labor.

Additionally and/or optionally, the system may use image sequences capturing how professionals (e.g., embryologists) manipulate biological samples using various culture tools to train a machine learning model for controlling the manipulator assembly. As such, the manipulator assembly may manipulate biological samples in ways that conform to manipulations conducted by professionals. Through automated manipulation, changes of environment conditions due to human presence may be reduced. Unmanned manipulation may not only avoid human errors that may result from working under time pressure but enable the system to be miniaturized in size, which can reduce resources (e.g., amount of airflow supplied) needed to control environment conditions within chambers. Advantageously, by integrating real time image capturing technologies and automated manipulator assemblies (e.g., robotic arms, cell pickers, or the like), the system may be remotely controlled by professionals (e.g., for ICSI, laser, or biopsy) to avoid human interference on a culture environment.

The foregoing aspects and many of the attendant advantages of this disclosure will become more readily appreciated as the same become better understood by reference to the following description, when taken in conjunction with the accompanying drawings.

Example System Block Diagrams

FIG. 1 is a block diagram of an automatic incubator system 100 which includes an incubator culture chamber 130, a manipulation chamber 120, an inlet chamber 140, an outlet chamber 150, an accessory chamber 160, an environment control subsystem 102, and an intelligent manipulator subsystem 104 in accordance with some embodiments of the present disclosure. As illustrated in FIG. 1, the automatic incubator system 100 may receive biological samples 110 from external environment through the inlet chamber 140. The automatic incubator system 100 may transport biological samples 110 to external environment through the outlet chamber 150. The intelligent manipulator subsystem 104 may manipulate the biological samples 110 in the manipulation chamber 120, the incubator culture chamber 130, the inlet chamber 140, the outlet chamber 150, and the accessory chamber 160. The environment control subsystem 102 may control environment conditions within the manipulation chamber 120, the incubator culture chamber 130, the inlet chamber 140, the outlet chamber 150, and the accessory chamber 160 for culturing the biological samples 110. Examples of the biological samples 110 include human cells, non-human cells, tissues, bacterial cells, stem cells, primary cells, mammalian oocytes (e.g., human oocytes), ovum, embryos, sperms, organoid, or the like. In some embodiments, each of the manipulation chamber 120, the incubator culture chamber 130, the inlet chamber 140, the outlet chamber 150, and the accessory chamber 160 may be structurally (e.g., separated by walls, doors, or other physical structures that can be movable) and/or fluidically (e.g., air from one chamber may not easily flow to another chamber) isolated from each other.

The inlet chamber 140 may include one or more inlet rooms that may be utilized to receive the biological samples 110 into the automatic incubator system 100. For example, the inlet chamber 140 may include a transfer room and an internal room that may be separated by a sliding door. The transfer room may serve as an intermediate space in which vessels that include the biological samples 110 can be cleaned or sterilized before entering the internal room, and/or conditions can be equilibrated with the internal room before the sliding door is opened. In some embodiments, the inlet chamber 140 may comply with International Standard Organization (ISO) Class 7 and/or 8 Cleanroom requirements. For example, the transfer room may comply with ISO Class 8 Cleanroom requirements and the internal room may comply with ISO Class 7 Cleanroom requirements.

The outlet chamber 150 can be utilized to accommodate transport pods that include the biological samples 110. Additionally, the outlet chamber 150 may be used to transport materials that are to be disposed outside the automatic incubator system 100. In some embodiments, the inlet chamber 140 may comply with International Standard Organization (ISO) Class 7 or 8 Cleanroom requirements. A sliding door (not shown in FIG. 1), such as a moveable closure, may be installed between the outlet chamber 150 and the manipulation chamber 120. In some embodiments, when a culture vessel is to be transported outside the automatic incubator system 100 through the outlet chamber 150, the environment control subsystem 102 may use the one-way airflow mode to equalize an environment condition within the outlet chamber 150 and an environment condition within the manipulation chamber 120. After the environment condition within the outlet chamber 150 and the environment condition within the manipulation chamber 120 are equalized (e.g., become at least substantially the same), the culture vessel may be transported through the manipulation chamber 120 into the outlet chamber 150.

The accessory chamber 160 may be utilized for various purposes. For example, the accessory chamber 160 may serve as space for cryopreservation in the context of IVF.

The accessory chamber 160 may accommodate immersion pods with liquid nitrogen inside for cryopreservation or other applications. In some embodiments, the accessory chamber 160 may comply with International Standard Organization (ISO) Class 7 or 8 Cleanroom requirements. A sliding door (not shown in FIG. 1) may be installed between the accessory chamber 160 and the manipulation chamber 120.

The incubator culture chamber 130 may store cell culture vessels or modules that include the biological samples 110 for cell growth. As noted above, environment conditions within the incubator culture chamber 130 may be controlled by the environment control subsystem 102 to maintain at a target condition such as temperature and air composition suitable for cell growth. In some embodiments, the incubator culture chamber 130 may comply with International Standard Organization (ISO) Class 6 or Federal Standard 209 Class 1000 requirements.

The manipulation chamber 120 may be utilized to accommodate at least a portion of the intelligent manipulator subsystem 104 for manipulating the biological samples 110. For example, a manipulator assembly (not shown in FIG. 1) of the intelligent manipulator subsystem 104 may manipulate the biological samples 110 inside the manipulation chamber 120. In some embodiments, the manipulation chamber 120 may comply with International Standard Organization (ISO) Class 6 or Federal Standard 209 Class 1000 requirements.

The intelligent manipulator subsystem 104 may include a combination of hardware, firmware, and software components and may be configured to automatically process biological samples 110 for culture without assistance of human professionals. As noted above, the intelligent manipulator subsystem 104 may manipulate (e.g., access, hold, place, transfer, move, process, or the like) biological samples 110 among the manipulation chamber 120, incubator culture chamber 130, inlet chamber 140, outlet chamber 150, and accessory chamber 160. In some embodiments, the intelligent manipulator subsystem 104 may utilize visual cameras of various resolutions along with thermal cameras to identify objects of interest for controlling a manipulator assembly (e.g., robotic arms) to automatically manipulate cells in culture vessels. The intelligent manipulator subsystem 104 may further use thermal imaging data from thermal cameras and information of identified objects to generate thermal control signals for controlling temperature at a particular spot in manipulation chamber 120, incubator culture chamber 130, inlet chamber 140, outlet chamber 150, and/or accessory chamber 160.

In some embodiments, the intelligent manipulator subsystem 104 may utilize machine learning techniques to analyze both image data from a visual camera and thermal imaging data from a thermal camera for identifying real-time information (e.g., identity, location, temperature, or the like) of objects (e.g., biological samples within a culture vessel, tips of pipettes, wells of Petri dishes, or the like) inside the manipulation chamber 120. The intelligent manipulator subsystem 104 may utilize computer vision techniques to process image data and thermal imaging data to derive or extract features (e.g., shape features) associated with objects that are or to be manipulated by a manipulator assembly.

The environment control subsystem 102 may include a combination of airflow and non-airflow control hardware, firmware, and software components and may be configured to control and maintain environment conditions in the manipulation chamber 120, the incubator culture chamber 130, the inlet chamber 140, the outlet chamber 150, and/or the accessory chamber 160 at a target condition. The target condition may specify a particular combination of temperature, humidity, air pressure, and/or air composition. It should be noted that parts of the environment control subsystem 102 may be distributed among the manipulation chamber 120, the incubator culture chamber 130, the inlet chamber 140, the outlet chamber 150, and/or the accessory chamber 160 while other parts of the environment control subsystem 102 may be deployed outside any of the above chambers.

In some embodiments, the environment control subsystem 102 may utilize airflow control mechanisms (e.g., generating and flowing air of certain quality to a chamber) in conjunction with non-airflow control mechanisms (e.g., heating or cooling a surface or a spot in the chamber) to effectively maintain or restore environment conditions in the manipulation chamber 120, the incubator culture chamber 130, the inlet chamber 140, the outlet chamber 150, and/or the accessory chamber 160 at the target condition. In some embodiments, the environment control subsystem 102 may use airflow control mechanisms to control air quality toward a desired quality (e.g., desired temperature, humidity, pressure, and/or air composition). Airflow control mechanisms may include filtering circulated air and/or supplying air inlets (e.g., air that is stored in an air tank and has not been circulated) to the manipulation chamber 120 or incubator culture chamber 130. The environment control subsystem 102 may further utilize non-airflow control mechanisms to control environment conditions. The non-airflow control mechanisms may include using heaters to heat certain surfaces within the manipulation chamber 120 or using air absorbers to absorb excess amount of oxygen, carbon dioxide, nitride, or other composition of air in the incubator culture chamber 130 or the manipulation chamber 120.

Additionally, the environment control subsystem 102 may apply distinct airflow control mechanisms to the manipulation chamber 120, the incubator culture chamber 130, the inlet chamber 140, the outlet chamber 150, and/or the accessory chamber 160 for controlling environment conditions in respective chambers. For example, the environment control subsystem 102 may utilize one-way airflow mode to provide air to the incubator culture chamber 130. Simultaneously, the environment control subsystem 102 may utilize semi-close or close airflow mode to provide air to the manipulation chamber 120, where a manipulator assembly automatically manipulate cells in cell culture tools (e.g., Petri dishes, vessels, pipettes, containers, or the like). Further, the environment control subsystem 102 may determine which airflow control modes (e.g., one-way, semi-close, close airflow) are suitable for corresponding chambers depending on various factors, such as sizes of chambers, types of cell culture that are conducted, remaining air inlets capacity inside air tanks, or the like. In some embodiments, the system may respond to user input indicating selection of individual modes. For example, the system may respond to wireless or wired communications from an application presenting a user interface. In some embodiments, the system may include a display which enables selection of the modes.

In some embodiments, the environment control subsystem 102 may adjust a target condition within the incubator culture chamber 130 or the manipulation chamber 120 based on types of applications and/or stages of cell culture (e.g., cell culture activities). For example, when utilizing the incubator culture chamber 130 for IVF treatments, the environment control subsystem 102 may set the target condition in the incubator culture chamber 130 to a temperature at about 37° C., 40% humidity, and an air composition with 5% to 6% oxygen, 5% to 6% carbon dioxide, and 88% to 90% nitrogen. In some examples, the target condition may include temperature at 35° C., 35.2° C., 35.4° C., 35.6° C., 35.8° C., 36° C., 36.2° C., 36.4° C., 36.6° C., 36.8° C., 37° C., 37.2° C., 37.4° C., 37.6° C., 37.8° C., 38° C., 38.2° C., 38.4° C., 38.6° C., 38.8° C., 39° C., or any range of values therebetween; humidity of 36%, 36.5%, 37%, 37.5%, 38%, 38.5%, 39%, 40%, 40.5%, 41%, 41.5%, 42%, 42.5%, 43%, 43.5%, 44%, or any range of values therebetween; and an air composition with 5% to 7% oxygen, 5% to 7% carbon dioxide, and 88% to 90% nitrogen. Additionally and/or optionally, the environment control subsystem 102 may further fine-tune the target condition at various stages of culture period. For example, the environment control subsystem 102 may change the carbon dioxide level between 5% to 10% at various stages (e.g., culture period of five days, culture period of ten days, how many days has elapsed after fertilization, or the like) of IVF treatments. The environment control subsystem 102 may also change the carbon dioxide level according to an external environment in which the automatic incubator system 100 is located. More specifically, when the automatic incubator system 100 is located in a low atmosphere pressure environment (e.g., in high altitude on earth, in aerospace, or the like), the environment control subsystem 102 may increase the carbon dioxide level from 5% toward 10%. For example, when the automatic incubator system 100 is in certain altitude above sea level (e.g., higher than 3000 meters), the environment control subsystem 102 may increase the carbon dioxide level to about, at least, or at least about 6%, 6.2%, 6.4%, 6.6%, 6.8%, 7.0%, 7.2%, 7.4%, 7.6%, 7.8%, 8.0%, 8.2%, 8.4%, 8.6%, 8.8%, 9.0%, or any range of values therebetween. Advantageously, the increased level of carbon dioxide may help maintain pH in a culture vessel to a desired level. As another example, when the automatic incubator system 100 is located in an environment where atmospheric pressure is higher (e.g., at sea level), the environment control subsystem 102 may adjust the carbon dioxide level to about 5%, 5.2%, 5.4%, 5.6%, 5.8%, 6.0%, 6.2%, 6.4%, 6.6%, or any range of values therebetween.

Example System Perspective Views

Figure 2A:
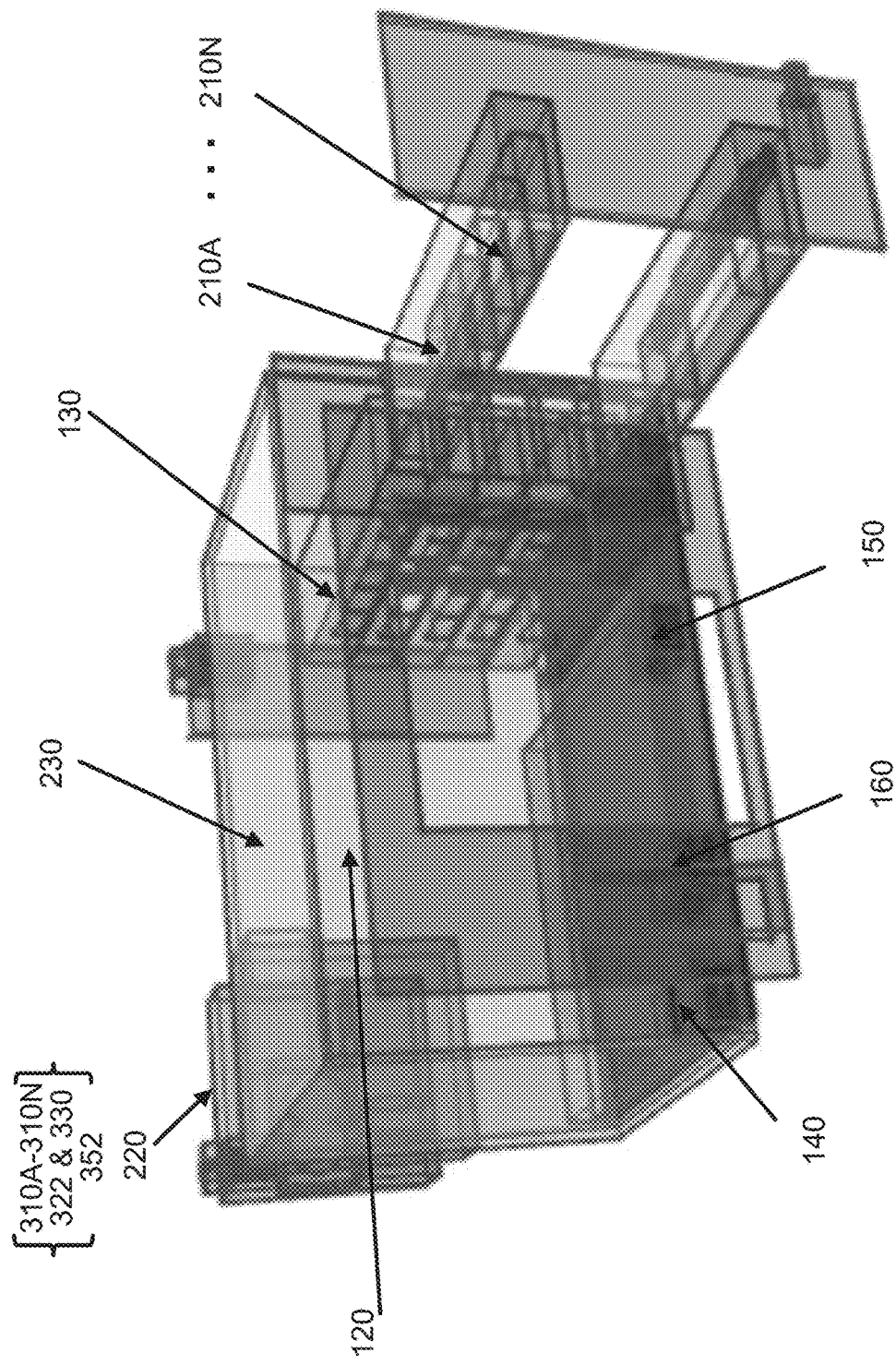
FIGS. 2A, 2B, 2C, 2D and 2E illustrate various views of the example automatic incubator system of FIG. 1 in accordance with some embodiments of the present disclosure.

FIGS. 2A, 2B, 2C and 2D illustrate example views of the automatic incubator system 100 of FIG. 1 in accordance with some embodiments of the present disclosure. FIG. 2A shows an example perspective view of the automatic incubator system 100 with the intelligent manipulator subsystem 104 and certain parts of the environment control subsystem 102 removed, and some parts disassembled. As illustrated in FIG. 2A, the automatic incubator system 100 includes a case 230 (e.g., a cell culture case) that structurally accommodates the incubator culture chamber 130, the manipulation chamber 120, the inlet chamber 140, the outlet chamber 150, and the accessory chamber 160. In some embodiments, the case 230 may be made of various materials, including heat insulation materials. For example, the case 230 can be made of materials that can provide robust structural support (e.g., stainless steel, aluminum, powder-coated steel, anodized aluminum, or the like) and materials that can provide thermal and/or air insulation (e.g., fiberglass, polyurethane foam, vacuum insulation panels, or the like). Additionally, space within the case 230 may be or close to airtight. By deploying the manipulation chamber 120, incubator culture chamber 130, inlet chamber 140, outlet chamber 150, and accessory chamber 160 inside the case 230, the automatic incubator system 100 can be highly integrated to advantageously allow various cell culture related operations to all be conducted automatically within the case 230. Compared with other systems where manipulation chamber and incubator chamber are not integrated within a physical structure (e.g., within the case 230) that provides isolation to external environments, the automatic incubator system 100 can also avoid fluctuations of environment conditions during transportation of biological samples. For example, as will be described below, the environment control subsystem 102 can maintain and/or adjust environment conditions within the manipulation chamber 120 and the incubator culture chamber 130 to be the same (e.g., same temperature, same humidity, same air composition, same pressure, and/or the like) while transporting the biological samples between the manipulation chamber 120 and incubator culture chamber 130.

In FIG. 2A, a housing 220 of the environment control subsystem 102 houses one or more air absorbers 352, at least parts of an air quality controller 320 (e.g., a quality control engine 322 and air filters 330 shown in FIG. 2B), and one or more air analyzers 310A-310N that will be described with respect to FIGS. 3A and 3B. As illustrated in FIG. 2A, the incubator culture chamber 130 includes one or more modules 210A-210N that can each include biological samples. Although FIG. 2A shows that the housing 220 is outside the case 230, it should be noted that the housing 220 and/or the environment control subsystem 102 may be entirely deployed inside the case 230 in other embodiments.

In some embodiments, the overall capacity (e.g., a capacity or volume of the case 230) of the manipulation chamber 120, the incubator culture chamber 130, the inlet chamber 140, the outlet chamber 150, and the accessory chamber 160 may be between 30 liter (L) to 500 L. In some embodiments, the overall capacity of the automatic incubator system 100 may be about or below 30 L, 80 L, 130 L, 180 L, 230 L, 280 L, 330 L, 380 L, 430 L, 480 L, 530 L, or any range of values therebetween. For example, excluding the housing 220 that houses parts of the air quality controller 320, the one or more air absorbers 352 and the one or more air analyzers 310A-310N, the automatic incubator system 100 may bear a shape of a rectangular cuboid, having about a length of 60 centimeter (cm), a width of 35 cm, and a height of 35 cm. The majority space of the automatic incubator system 100 may be occupied by the manipulation chamber 120 and the incubator culture chamber 130. As noted above, the incubator culture chamber 130 may include a plurality of modules 210A-210N that may accommodate various biological samples.

As illustrated in FIG. 2A, some parts of the environment control subsystem 102 may be deployed outside the manipulation chamber 120, the incubator culture chamber 130, the inlet chamber 140, the outlet chamber 150, and the accessory chamber 160. For example, parts of the air quality controller 320 (e.g., the quality control engine 322) and the one or more air analyzers 310A-310N are shown to be housed in the housing 220 deployed outside and adjacent to the manipulation chamber 120. Other parts of the environment control subsystem 102 (e.g., air reservoir 326, air heater 328, airflow assemblies 340A-340N) may be deployed inside the manipulation chamber 120, the incubator culture chamber 130, the inlet chamber 140, the outlet chamber 150, and/or the accessory chamber 160.

Figure 2B:
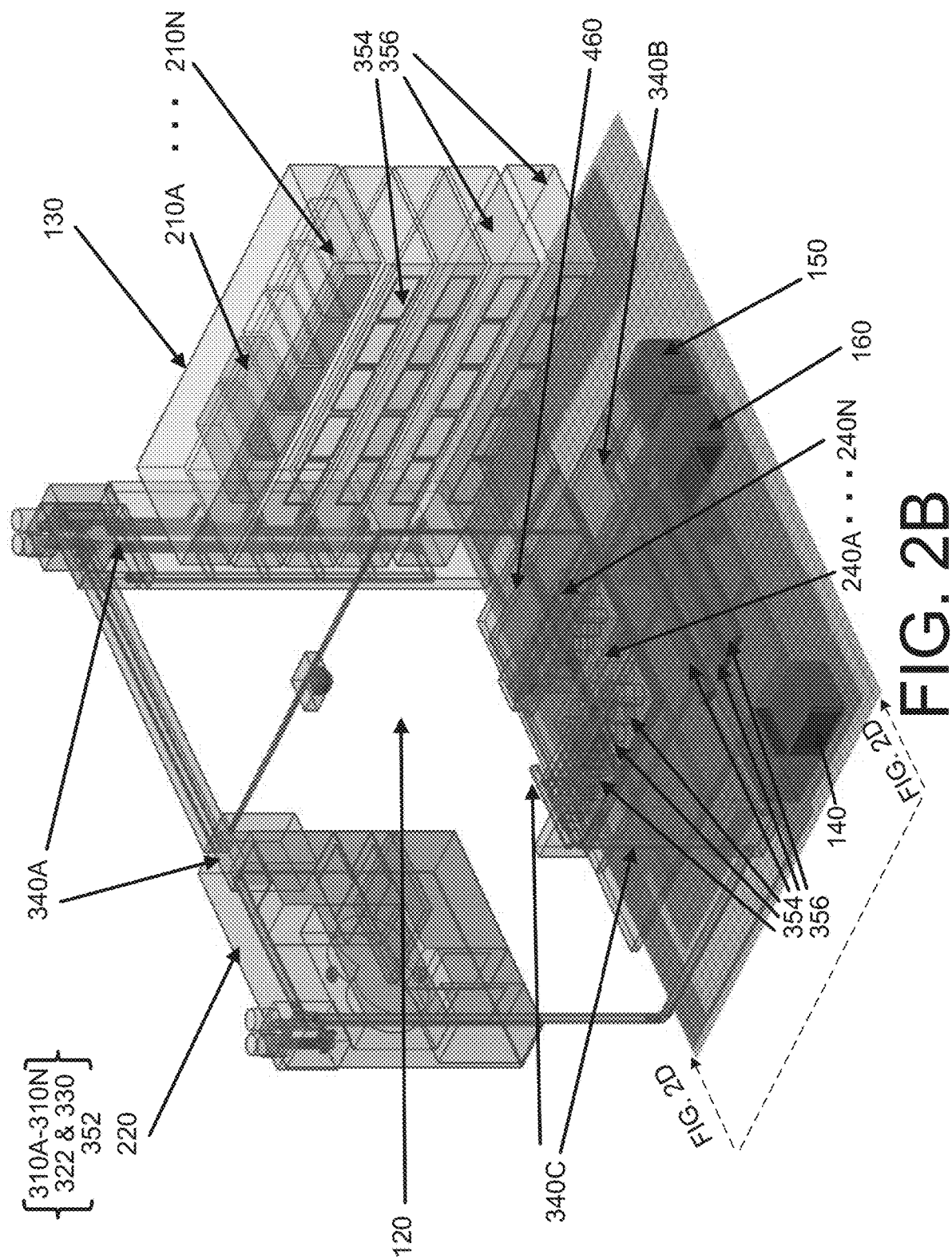

FIG. 2B illustrates an example perspective view of the automatic incubator system 100 of FIG. 1 with certain parts (e.g., the case 230) removed. As illustrated in FIG. 2B, the environment control subsystem 102 includes an airflow assembly 340A, an airflow assembly 340B, an airflow assembly 340C, sensors 356, and heaters 354. The airflow assembly 340A can direct air to flow between the housing 220 and the incubator culture chamber 130. For example, air generated by the air quality controller 320 may flow from the airflow assembly 340A to the incubator culture chamber 130. As another example, excess oxygen, carbon dioxide, and/or nitrogen inside the incubator culture chamber 130 may be directed to the air absorbers 352 to be absorbed through the airflow assembly 340A. The airflow assembly 340B can direct air to flow between the housing 220 and the inlet chamber 140, the outlet chamber 150, and/or the accessory chamber 160. The airflow assembly 340C can direct air to flow between the housing 220 and the manipulation chamber 120.

In FIG. 2B, the manipulation chamber 120 is shown to include one or more modular blocks 240A-240N on a working table 460. The one or more modular blocks 240A-240N can each accommodate various biological samples. Each of the one or more modular blocks 240A-240N can house a heater 354 and a sensor 356 that can be utilized to sense and adjust temperature associated with the one or more modular blocks 240A-240N.

As illustrated in FIG. 2B, the airflow assembly 340A may be connected to the air quality controller 320 and/or the one or more air analyzers 310A-310N on one end, and extend into the incubator culture chamber 130 on the other end. The airflow assembly 340B may be connected to the air quality controller 320 on one end, and extend into the inlet chamber 140, outlet chamber 150, and/or accessory chamber 160 on the other end. The airflow assembly 340C may be connected to the air quality controller 320 on one end and extend into the manipulation chamber 120 on the other end.

More specifically, in some embodiments each of the airflow assembly 340A, airflow assembly 340B, and airflow assembly 340C may include air valves and air tubes that can be utilized by the environment control subsystem 102 to maintain environment conditions in various chambers through airflow control mechanisms. For example, the airflow assembly 340A may include at least two air tubes that are substantially parallel to each other. One, or one or more, air tube(s) of the airflow assembly 340A may be utilized to direct air, or other gas, inside the incubator culture chamber 130 to the air analyzer 310A and the air quality controller 320 for analyzing air quality (e.g., temperature, humidity, composition, and/or pressure). The other air tube(s) of the airflow assembly 340A may be utilized to flow air processed (e.g., filtered, circulated, or the like) by the air quality controller 320 based on analysis of the air analyzer 310A into the incubator culture chamber 130. The environment control subsystem 102 may similarly utilize airflow assembly 340B to direct air for sample and analysis, and utilize airflow assembly 340C to direct air for sample and analysis.

As shown in FIG. 2B, the sensors 356 and the heaters 354 may be deployed at various parts of the incubator culture chamber 130. For example, each of the sensors 356 and each of the heaters 354 may be deployed inside each of the modules 210A-210N to sense temperature within each module for temperature adjustment. Although FIG. 2B illustrates that the sensors 356 and the heaters 354 are deployed inside parts of the incubator culture chamber 130 and the manipulation chamber 120, it should be noted that the sensors 356 and the heaters 354 may be deployed inside any other spots (e.g., on certain locations of the working table 460) or other chambers of the automatic incubator system 100. In some embodiments, each of the sensors 356 may be paired with each of the heaters 354 for detecting and heating temperature associated with a particular spot inside the automatic incubator system 100. It should be noted that each of the heaters 354 can also be embodied as a temperature adjustment device that can both increase and decrease temperature. Components of the environment control subsystem 102 will be further described with detail in FIGS. 3A and 3B.

Figure 2C:
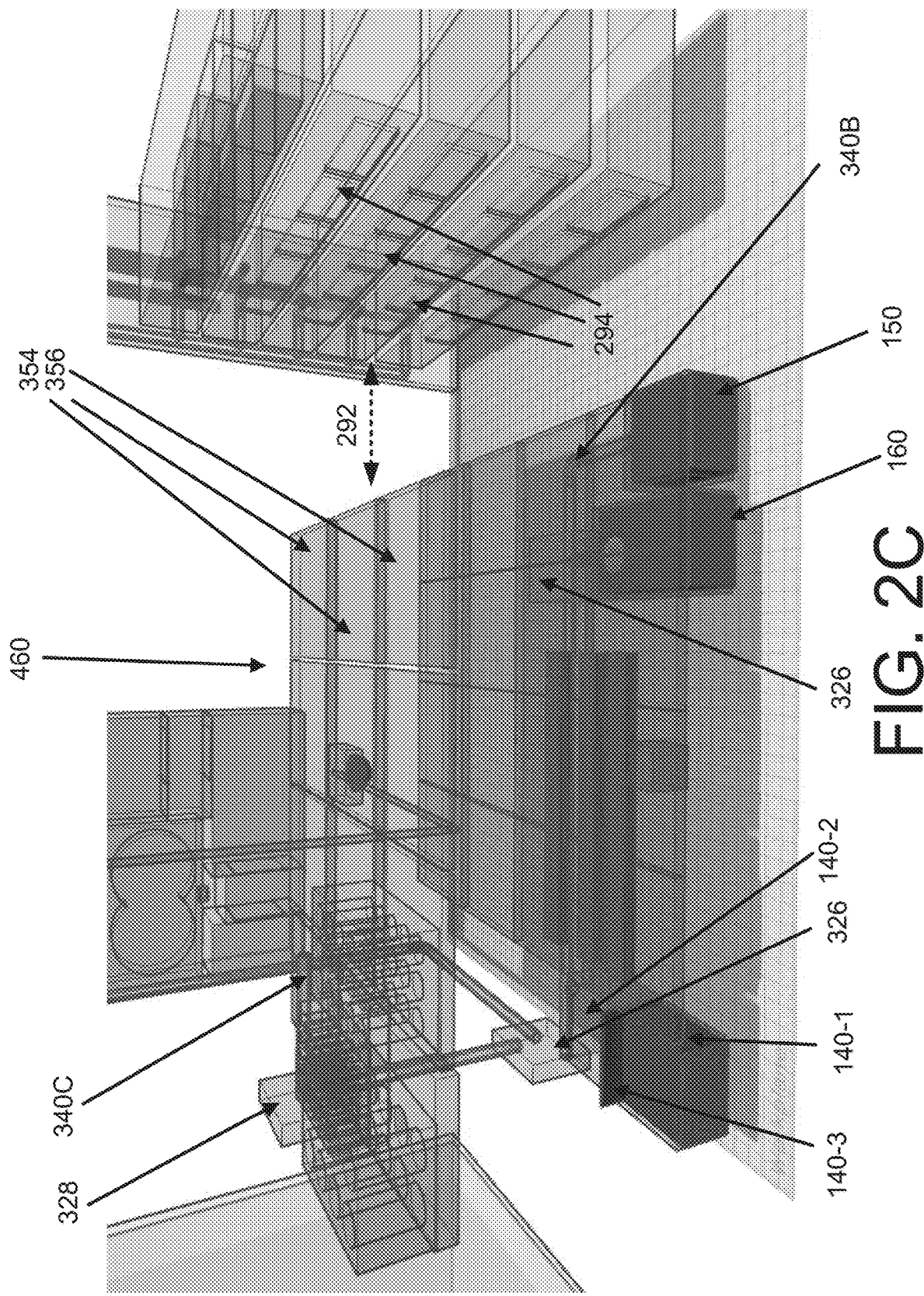

FIG. 2C illustrates an example perspective view of certain parts of the automatic incubator system 100. As illustrated in FIG. 2C, some of the sensors 356 and some of the heaters 354 of the environment control subsystem 102 are deployed on the working table 460. Further, the inlet chamber 140 may include a transfer room 140-1, and an internal room 140-2. The transfer room 140-1 and the internal room 140-2 may be separated by a sliding door 140-3. As noted above, the transfer room 140-1 may serve as an intermediate space in which vessels that include the biological samples 110 can be cleaned or sterilized before entering the internal room 140-2, and/or conditions can be equilibrated with the internal room 140-2 before the sliding door 140-3 is opened. In some embodiments, biological samples within culture vessels may be received by the transfer room 140-1. Inside the transfer room 140-1, the culture vessels may be air-showered (e.g., for cleaning or sterilization purposes) using the one-way airflow mode implemented by the environment control subsystem 102. The air-showered culture vessels may then be transported into the internal room 140-2. The environment control subsystem 102 may equalize an environment condition within the internal room 140-2 and an environment condition within the manipulation chamber 120 using the one-way airflow mode or another airflow mode (e.g., semi-close or close airflow mode), before the culture vessels are transported to the manipulation chamber 120 and/or the incubator culture chamber 130.

Advantageously, through equilibrating or equalizing environment conditions within the inlet chamber 140, manipulation chamber 120, incubator culture chamber 130, and/or accessory chamber 160 before transportation of culture vessels (e.g., the one or more modules 210A-210N that include biological samples) starts, the automatic incubator system 100 may comply with more stringent clean room requirements. More specifically, compared with other systems where isolation with external environments is less thorough or environment conditions are not equalized or not in equilibrium during transportation of biological samples, the automatic incubator system 100 may more accurately maintain environment conditions within the case 230 at desired or optimized conditions for particular cell culture activities. Through the coordination of components (e.g., the transfer room 140-1, internal room 140-2, the airflow assemblies 340A-340N, heaters 354, air absorbers 352, or the like) of the automatic incubator system 100, the automatic incubator system 100 may also enable the manipulation chamber 120, incubator culture chamber 130, inlet chamber 140, outlet chamber 150, and/or accessory chamber 160 to comply with more advanced clean room requirements under ISO Class 7, ISO Class 6, and/or ISO Class 5.

In FIG. 2C, the air reservoirs 326 and the air heater 328 are connected to the airflow assembly 340B and the airflow assembly 340C. In some embodiments, the one or more modules 210A-210N can be transported into, out of, and/or among the manipulation chamber 120, incubator culture chamber 130, inlet chamber 140, outlet chamber 150, and accessory chamber 160 for cell culture related activities. For example, the one or more modules 210A-210N can be retrieved from the incubator culture chamber 130 for processing or manipulations (e.g., by a manipulator assembly 450 that will be discussed below) within the manipulation chamber 120 along the directions 292. More specifically, the incubator culture chamber 130 may include structures 294, such as movable structures, (e.g., one or more sliding doors, drawers, or the like) that can be opened (e.g., by the manipulator assembly 450) to allow the manipulator assembly 450 to retrieve the one or more modules 210A-210N from the incubator culture chamber 130 for manipulation. In some embodiments, before the structures 294 open, the environment control subsystem 102 can adjust (e.g., through the airflow assembly 340A, airflow assembly 340C, heaters 354, and/or air absorbers 352) environment conditions within the incubator culture chamber 130 and the manipulation chamber 120 toward the same target environment condition. As such, environment conditions within the incubator culture chamber 130 and the manipulation chamber 120 can be the same or equilibrated when the structures 294 open, which can avoid fluctuations of environment conditions within the incubator culture chamber 130 and the manipulation chamber 120 during the transportation, moving, and/or retrieval of biological samples for manipulation, processing, culture, and/or storage.

As noted above, when the structures 294 are closed, the manipulation chamber 120 and the incubator culture chamber 130 can be structurally and/or fluidically isolated from each other to enable the environment control subsystem 102 to have the flexibility to separately control an environment condition within the manipulation chamber 120 and another environment condition within the incubator culture chamber 130. Advantageously, this provides the automatic incubator system 100 the capability to maintain different environment conditions within the manipulation chamber 120 and the incubator culture chamber 130 for different applications or cell culture activities.

In some embodiments, the structures 294 can be opened and closed by the manipulator assembly 450, and/or otherwise controlled by the automatic incubator system 100 to open and close. For example, the manipulator assembly 450 may push a button on a structure 294 to trigger the structure 294 to move (e.g., through operations of motors) along a track to isolate or fluidically connect the manipulation chamber 120 and the incubator culture chamber 130. In some embodiments, the structures 294 may include and/or be associated with mechanical seals (e.g., gaskets) to prevent air exchange between the manipulation chamber 120 and the incubator culture chamber 130 when the structures 294 are closed. As such, the manipulation chamber 120 and the incubator culture chamber 130 can be fluidically isolated from each other to allow separate environment condition control within the manipulation chamber 120 and the incubator culture chamber 130 when the structures 294 are closed. It should be noted that the environment control subsystem 102 can also separately control environment conditions within the inlet chamber 140, outlet chamber 150, and/or the accessory chamber 160. As will be described with respect to FIG. 3B, the air reservoir 326 may be utilized to quickly restore air composition in the manipulation chamber 120, incubator culture chamber 130, inlet chamber 140, outlet chamber 150, and/or accessory chamber 160 when air composition deviates from a desired air composition greater than a threshold.

Figure 2D:
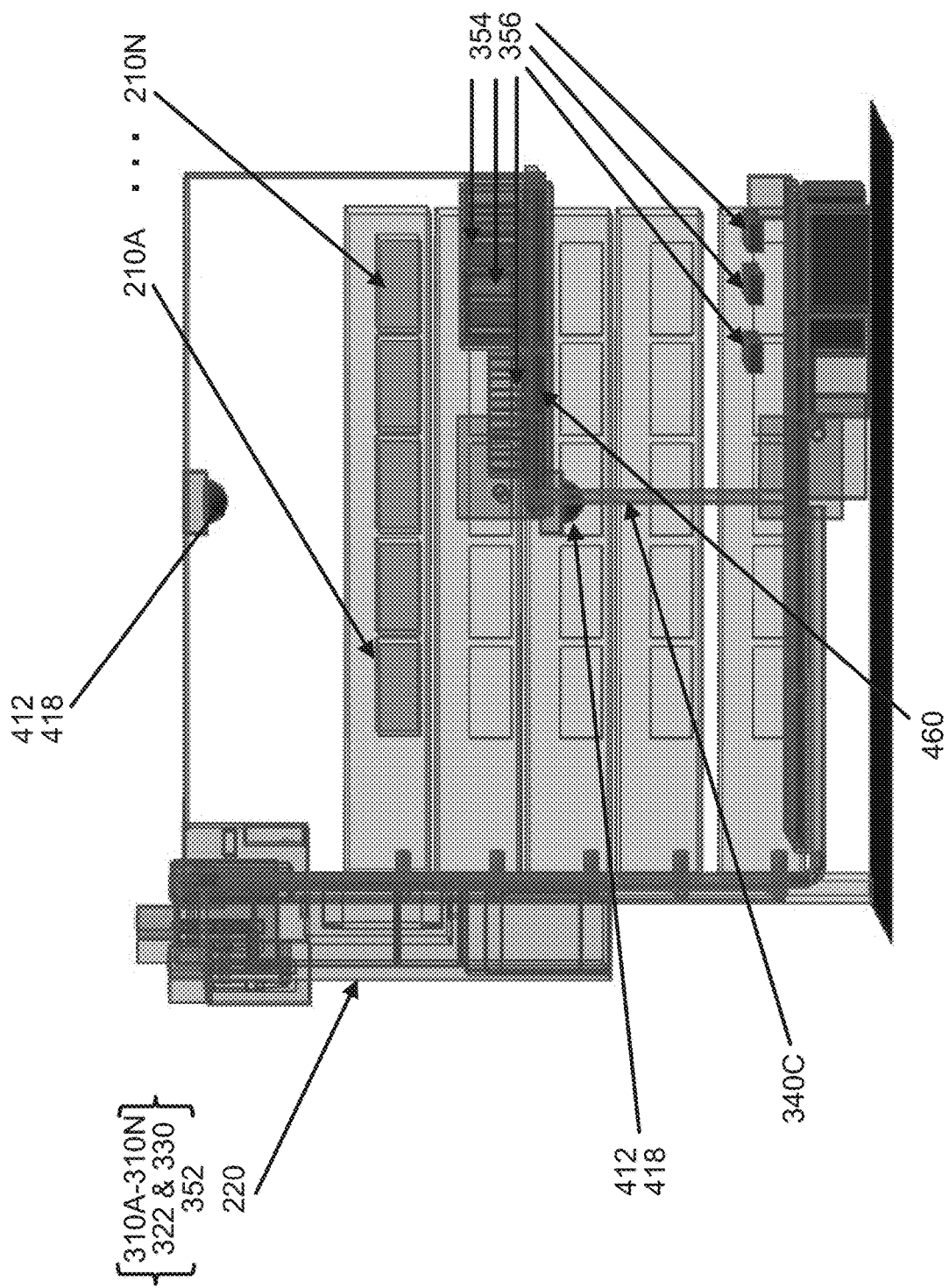

FIG. 2D illustrates an example cross-section view of the automatic incubator system 100 taken along the lines FIG. 2D-FIG. 2D of FIG. 2B. FIG. 2D illustrates that the sensors 356 and the heaters 354 are deployed on or below the working table 460. FIG. 2D further illustrates visual camera(s) 412 and thermal camera(s) 418 that will be described with greater detail in FIG. 2E.

Figure 2E:
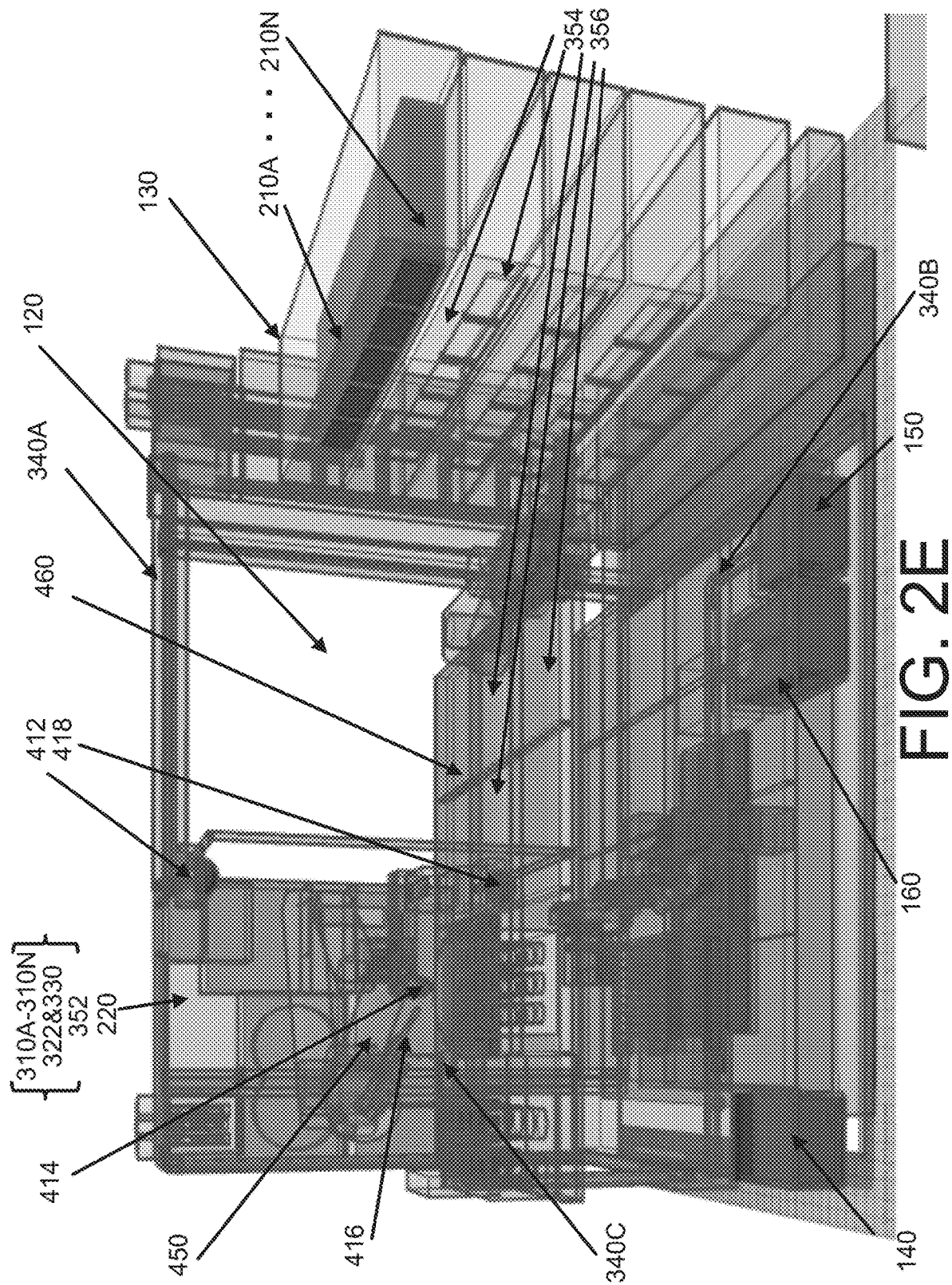

FIG. 2E illustrates an example perspective view of the automatic incubator system 100 in accordance with some embodiments of the present disclosure. In some embodiments, FIG. 2E shows a full integration of the automatic incubator system 100 except that the case 230 is removed. As illustrated in FIG. 2E, the intelligent manipulator subsystem 104 includes a visual camera 412, a thermal camera 418, a microscopic camera 414, a microscopic front camera 416, a working table 460, and a manipulator assembly 450 deployed on the working table 460. The intelligent manipulator subsystem 104 may utilize the visual camera 412, the thermal camera 418, the manipulator assembly 450 to automatically manipulate biological samples. The visual camera 412 and the thermal camera 418 may be deployed around a ceiling associated with the manipulation chamber 120 or a surface of the working table 460. In some embodiments, the visual camera 412 and the thermal camera 418 may be movable (e.g., along one or more rails) or fixed at particular locations.

Although FIG. 2E illustrates the visual camera 412 and the thermal camera 418 as being integrated with each other, in some embodiments they may be separately installed, or otherwise included, on other parts. For example, they may be attached to the case 230 inside the manipulation chamber 120 of the automatic incubator system 100. Further, the visual camera 412 and the thermal camera 418 may each move along a rail to broaden visual and thermal detection coverages inside the automatic incubator system 100. The intelligent manipulator subsystem 104 may control the manipulator assembly 450 to manipulate the biological samples 110 based on thermal imaging data and image data provided by the visual camera 412 and the thermal camera 418. As noted above, the manipulator assembly 450 may retrieve biological samples from the incubator culture chamber 130 to manipulate and transport manipulated biological samples back into (e.g., through the structures 294) the incubator culture chamber 130. Components of the intelligent manipulator subsystem 104 and manipulations that can be performed on the biological samples will be described with greater detail in FIGS. 4, 5A, and 5B.

In operation, the environment control subsystem 102 may utilize the air quality controller 320, the airflow assembly 340A, the airflow assembly 340B, and the airflow assembly 340C to implement various airflow modes, such as one-way, semi-close, and close airflow modes. For example, the environment control subsystem 102 may utilize the airflow assembly 340A to implement one-way airflow mode in the incubator culture chamber 130 to periodically supply air inlets stored in air tanks that may be housed inside the housing 220. The environment control subsystem 102 may concurrently utilize the airflow assembly 340C to implement semi-close or close airflow mode in the manipulation chamber 120 to periodically circulate at least some air within the manipulation chamber 120. As another example, the environment control subsystem 102 may utilize close airflow mode both for controlling air quality in the manipulation chamber 120 and the incubator culture chamber 130.

In some embodiments, the rate at which air inlets flow into a chamber or air in the chamber is circulated may be between 0.05 to 20 times per hour, or any range of values therebetween. For example, under the semi-close or close airflow modes, the environment control subsystem 102 may set the total air change per hour (TACH) to 0.1 to 15 times per hour, and set fresh air change per hour (FACH) to 0.1 to 3 times per hour. Under the one-way airflow mode, the environment control subsystem 102 may set the TACH to 0.1 to 15 times per hour. Additionally, the environment control subsystem 102 may adjust the TACH and/or FACH based on the airflow modes. For example, the environment control subsystem 102 may decrease both the TACH and FACH when switching from semi-close airflow mode to close airflow mode.

As noted above, the environment control subsystem 102 may set airflow modes for respective chambers based on various factors. For example, when the incubator culture chamber 130 is utilized for certain culture activity (e.g., to culture unknown cells or cells that may be toxic), the environment control subsystem 102 may utilize close airflow mode to control air quality inside the incubator culture chamber 130 to avoid air leakage from the incubator culture chamber 130 to other chambers and/or external environments. For example, a user may specify (e.g., through a user interface 800 of FIG. 8) that a culture activity that is conducted inside the incubator culture chamber 130 relates to culturing toxic cells. As another example, a culture activity that is conducted inside a chamber may be determined automatically by the intelligent manipulator subsystem 104 (e.g., using the camera assembly 410 and/or thermal camera 418) that will be discussed below. Based on the culture activity specified by the user or determined by the intelligent manipulator subsystem 104, the environment control subsystem 102 can determine that close airflow mode should be utilized to control air quality inside the incubator culture chamber 130 to avoid air leakage from the incubator culture chamber 130 to other chambers and/or external environments. As such, the automatic incubator system 100 may not only protect biological samples from adverse influence associated with external environments, but also protect external environments from biological samples that may be toxic or harmful to external environments. Under the close airflow mode where air within a particular chamber is fully circulated, the environment control subsystem 102 may utilize components such as air absorbers 352 to adjust or control air composition. But if a culture activity that is conducted inside a chamber (e.g., the manipulation chamber 120 and the incubator culture chamber 130) does not involve cells that may be toxic or harmful to external environments, the environment control subsystem 102 may determine that one-way airflow mode or semi-close airflow mode can be used to control air quality inside the chamber.

In some embodiments, one cell culture activity can be conducted inside the incubator culture chamber 130 and another cell culture activity can be conducted inside the manipulation chamber 120. For example, the incubator culture chamber 130 may culture human oocytes while the manipulator assembly 450 inside the manipulation chamber 120 may manipulate human skin tissues or mammalian oocytes. In this example, by separately controlling respective environments (e.g., using different airflow modes) within the manipulation chamber 120 and incubator culture chamber 130 can advantageously allow the automatic incubator system 100 to conduct different culture activities at respective optimized environment conditions.

As another example, when provision of air inlets is abundant (e.g., remaining capacity inside air tanks that store air inlets are high) and/or when more straightforward (e.g., less air circulation or air quality analysis) airflow control mechanism is desired, the environment control subsystem 102 may utilize one-way airflow mode to control air quality in one or more of the manipulation chamber 120, the incubator culture chamber 130, the inlet chamber 140, the outlet chamber 150, and the accessory chamber 160. As yet another example, the environment control subsystem 102 may select airflow modes for a chamber based on a size of the chamber. For example, the environment control subsystem 102 may utilize one-way airflow mode to provide air to a chamber when a size of the chamber is smaller than a predetermined value (e.g., 3 L). Additionally and/or optionally, an airflow mode for a chamber may be set by a user. For example, the user may utilize the user interface 800 of FIG. 8 to set the airflow mode for the chamber.

In some embodiments, the environment control subsystem 102 may control air qualities inside each chamber (e.g., the manipulation chamber 120, the incubator culture chamber 130, the inlet chamber 140, the outlet chamber 150, and the accessory chamber 160) that can be different from each other due to various operations (e.g., heat dissipated by a manipulator assembly) or processes (e.g., air released or consumed by cells during growth, thawing of liquid nitrogen) performed in respective chambers toward a desired quality. For example, in the context of administering cell culture for IVF treatments, the environment control subsystem 102 may detect and analyze air qualities to control air quality in each chamber toward temperature at 37° C., 40% humidity, and an air composition with 5% oxygen, 6% carbon dioxide, and 89% nitrogen. As such, each of the manipulation chamber 120, the incubator culture chamber 130, the inlet chamber 140, the outlet chamber 150, and the accessory chamber 160 may be controlled to restore to the same environment conditions from different environment conditions.

Besides using airflow control mechanism to control environment conditions, the environment control subsystem 102 may utilize non-airflow control mechanisms such as the air absorbers 352, the heaters 354 and the sensors 356 to control environment conditions within each chamber. For example, when the sensors 356 detect that temperate at a surface in the manipulation chamber 120 is lower than a desired temperature, the environment control subsystem 102 may activate a heater 354 that is close to the surface to heat the surface. In some embodiments, the heaters 354 may be integrated with some cooling elements so as to be capable of both increasing and decreasing temperature associated with a chamber. As another example, the environment control subsystem 102 may activate the air absorbers 352 to absorb oxygen, nitrogen, carbon dioxide, or the like in the air to adjust air composition in a particular chamber toward a desired composition.

Figure 2F:
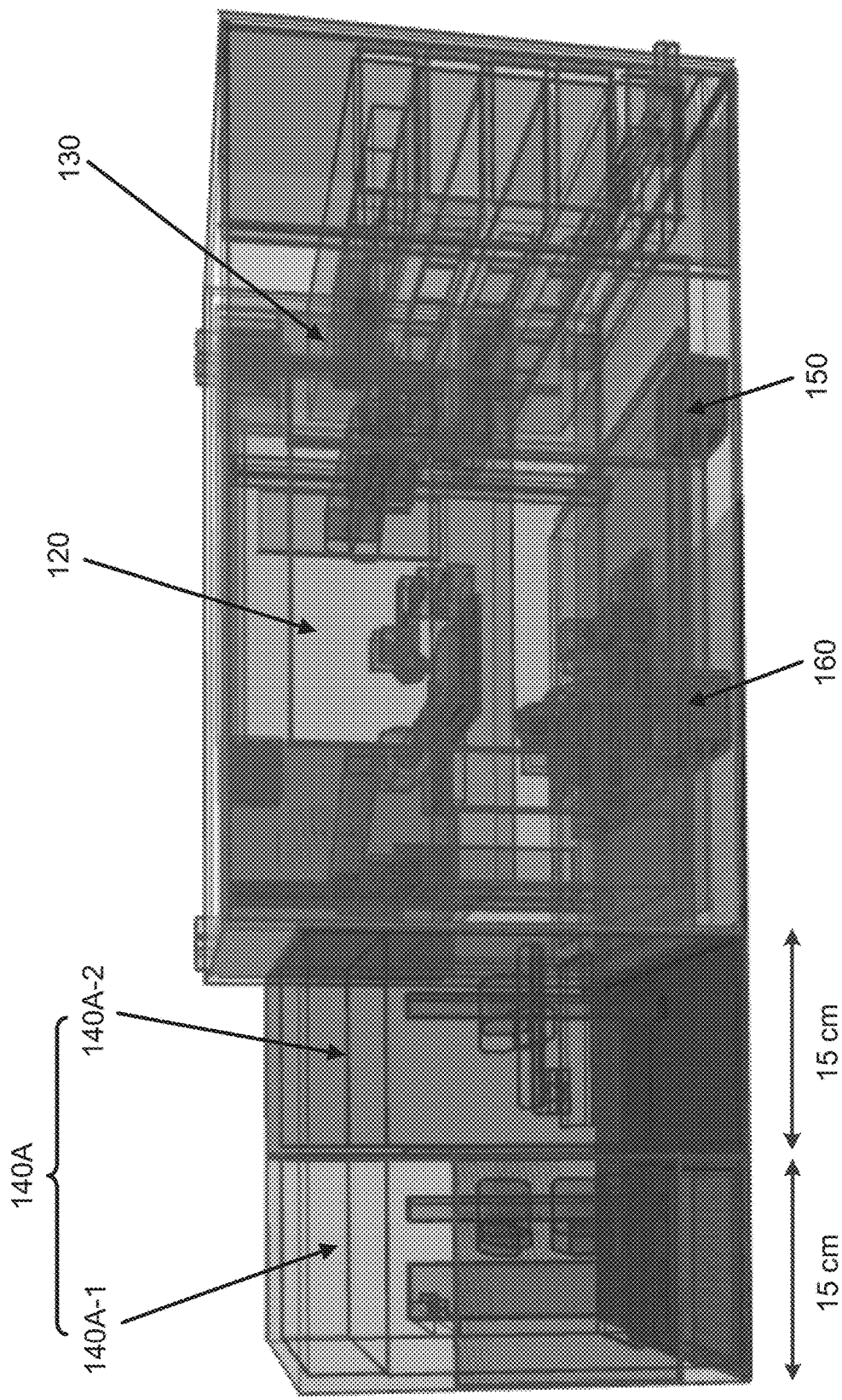
FIG. 2F illustrates an example perspective view of an automatic incubator system in accordance with some embodiments of the present disclosure.

FIG. 2F illustrates an example perspective view of an automatic incubator system 100A in accordance with some embodiments of the present disclosure. Unless otherwise noted, the automatic incubator system 100A functions similarly and is structurally similar to the automatic incubator system 100 as illustrated in FIGS. 2A-2E. For example, components and chambers of FIG. 2F can function and be structurally the same as or generally similar to like-numbered components and chambers of FIGS. 2A-2E. As shown in FIG. 2F, the automatic incubator system 100A structurally includes a manipulation chamber 120, an incubator culture chamber 130, an outlet chamber 150, an accessory chamber 160, and an inlet chamber 140A that includes a transfer room 140A-1 and an internal room 140A-2.

In contrast to the inlet chamber 140 of the automatic incubator system 100, the inlet chamber 140A may be of larger sizes than the inlet chamber 140. For example, the transfer room 140-1 and the internal room 140-2 may be each to bear a shape of a rectangular cuboid, having a length between 4 cm to 6 cm, a width between 4 cm to 6 cm, and a height between 2 cm to 4 cm. The transfer room 140A-1 and the internal room 140A-2 may each have a height between 25 cm to 35 cm (e.g., 30 cm), a width between 25 cm to 35 cm (e.g., 30 cm), and a length between 10 cm to 20 cm (e.g., 15 cm). Advantageously, with larger sizes, the transfer room 140A-1 and the internal room 140A-2 may allow the automatic incubator system 100A to receive biological samples and/or modules (e.g., blood packs) with larger sizes. In some examples, the transfer room 140A-1 may comply with ISO Class 8 Cleanroom requirements. The internal room 140A-2 may comply with ISO Class 7 Cleanroom requirements. The manipulation chamber 120 may comply with ISO Class 5 Cleanroom requirements. The incubator culture chamber 130 may comply with ISO Class 5 Cleanroom requirements.

Example Block Diagrams of Environment Control Subsystem

Figure 3A:
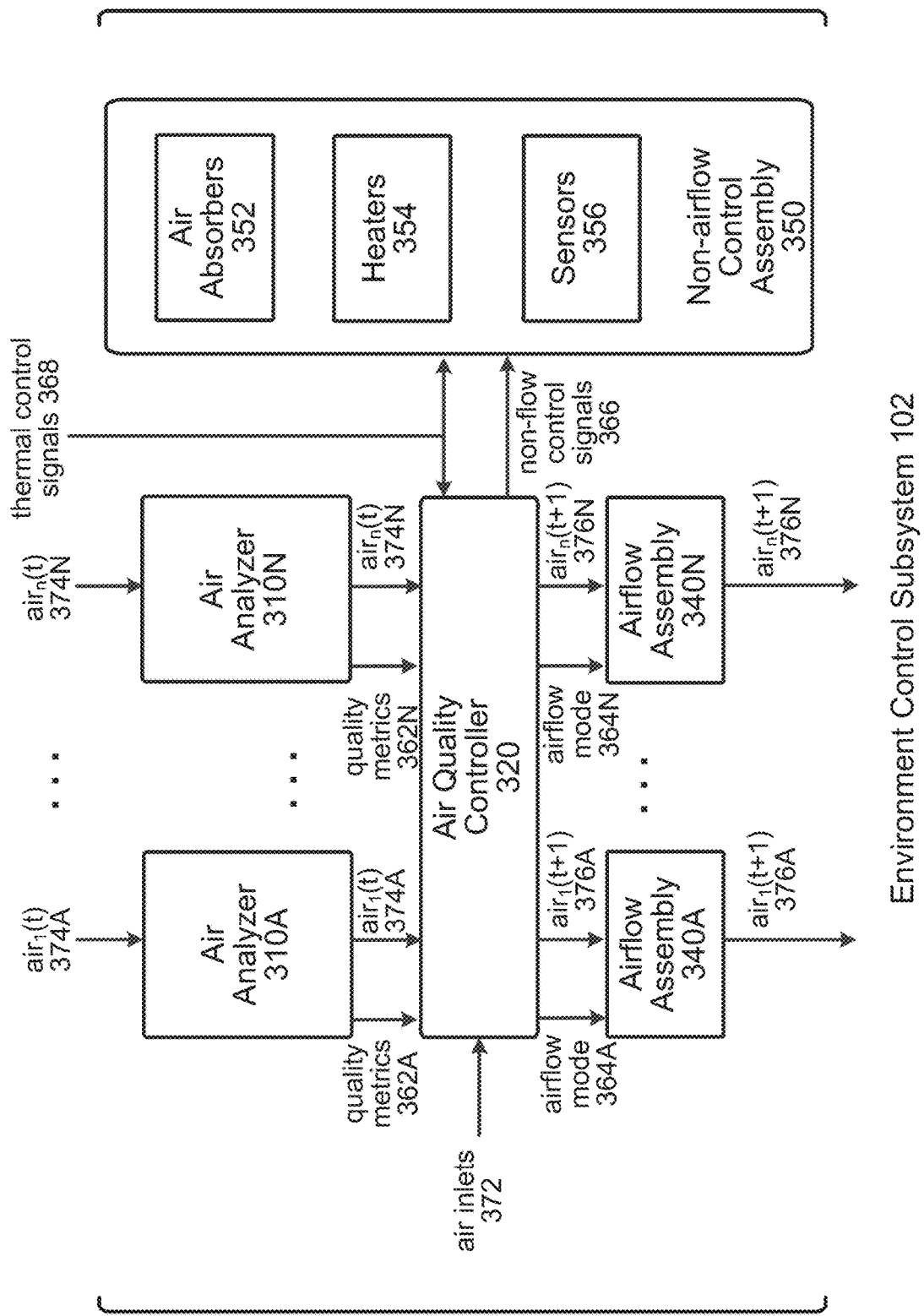
FIG. 3A is a block diagram of the environment control subsystem of FIG. 1 in accordance with some embodiments of the present disclosure.

FIG. 3A is a block diagram of the environment control subsystem 102 of FIG. 1 in accordance with some embodiments of the present disclosure. As illustrated in FIG. 3A, the environment control subsystem 102 includes the one or more air analyzers 310A-310N, the air quality controller 320, the one more airflow assemblies 340A-340N, and the non-airflow control assembly 350 that includes the air absorbers 352, the heaters 354 and the sensors 356. Both the air quality controller 320 and the non-airflow control assembly 350 may control environment conditions within the automatic incubator system 100 based on thermal control signals 368 that are generated as described in FIG. 4 with respect to the intelligent manipulator subsystem 104.

As shown in FIG. 3A, the air analyzer 310A may be paired with the airflow assembly 340A to detect and control air quality inside the incubator culture chamber 130, and so on (e.g., the air analyzer 310N may be paired with the airflow assembly 340N to control another chamber). More specifically, the air analyzer 310A may analyze the $air_1(t)$ 374A that is sampled and directed by the airflow assembly 340A from air inside the incubator culture chamber 130. The air analyzer 310A may thus determine air quality such as pressure, humidity, temperature, and/or composition in the incubator culture chamber 130 at a particular time instant. Based on the analysis, the air analyzer 310A may generate quality metrics 362A that are indicative of air quality (e.g., temperature, humidity, pressure, and/or composition) in the incubator culture chamber 130.

Based on the quality metrics 362A, the $air_1(t)$ 374A, air inlets 372, and/or the airflow mode 364A, the air quality controller 320 may generate subsequent air, e.g., $air_1(t+1)$ 376A, that is to be provided to the incubator culture chamber 130 by the airflow assembly 340A. For example, when the air quality controller 320 determines that the airflow mode 364A for the incubator culture chamber 130 is the one-way airflow mode, the air quality controller 320 may generate the $air_1(t+1)$ 376A using the air inlets 372 (e.g., air that is stored in an air tank housed in the housing 220 outside the incubator culture chamber 130). The air inlets 372 may be optionally filtered (e.g., through volatile organic compounds (VOC) filtering) to generate the $air_1(t+1)$ 376A. In this example, the air quality controller 320 may not circulate the $air_1(t)$ 374A for generating the $air_1(t+1)$ 376A. As another example, when the air quality controller 320 determines that the airflow mode 364A is the semi-close airflow mode, the air quality controller 320 may generate the $air_1(t+1)$ 376A based on the air inlets 372 and the $air_1(t)$ 374A. More specifically, the air quality controller 320 may filter the $air_1(t)$ 374A to be mixed with the air inlets 372 to generate the $air_1(t+1)$ 376A. As another example, when the air quality controller 320 determines that the airflow mode 364A is the close airflow mode, the air quality controller 320 may generate the $air_1(t+1)$ 376A based on the $air_1(t)$ 374A and without using the air inlets 372.

Based on the airflow mode 364A, the air quality controller 320 may control the airflow assembly 340A to flow the $air_1(t+1)$ 376A to the incubator culture chamber 130. For example, when the airflow mode 364A is the close airflow mode, the air quality controller 320 may control the airflow assembly 340A to let the $air_1(t+1)$ 376A flow to the incubator culture chamber 130 at a lower frequency (e.g., under lower TACH and FACH).

Additionally, based on the quality metrics 362A-362N, the air quality controller 320 may generate non-flow control signals 366 to control the non-airflow control assembly 350 to adjust environment conditions within chambers of the automatic incubator system 100. For example, when the quality metrics 362A indicates that temperature in the incubator culture chamber 130 is lower than a desired level, the air quality controller 320 may generate the non-flow control signals 366 to cause a heater 354 inside the incubator culture chamber 130 to heat up temperature. As another example, when the quality metrics 362A indicates that carbon dioxide level inside the incubator culture chamber 130 is at a level (e.g., 15%) higher than a desired level (e.g., 6%), the air quality controller 320 may generate non-flow control signals 366 to activate the air absorbers 352 to absorb carbon dioxide inside the incubator culture chamber 130 through the airflow assembly 340A (e.g., an air tube of the airflow assembly 340A that can direct carbon dioxide to the air absorbers 352 to be absorbed).

In some embodiments, a level of activation of the air absorbers 352 may depend upon the airflow modes 364A through 364N. For example, when the airflow mode 364A is the close airflow mode, the air quality controller 320 may generate the non-flow control signals 366 to fully activate (e.g., 100% activation) the air absorbers 352 to absorb carbon dioxide in the incubator culture chamber 130. When the airflow mode 364A is the semi-close airflow mode, the air quality controller 320 may generate the non-flow control signals 366 to partially activate (e.g., 50% activation) the air absorbers 352 to absorb carbon dioxide in the incubator culture chamber 130. When the airflow mode 364A is the one-way airflow mode, the air quality controller 320 may not activate the air absorbers 352 to absorb carbon dioxide in the incubator culture chamber 130. Rather, the air quality controller 320 may cause the airflow assembly 340A to flow the $air_1(t+1)$ 376A into the incubator culture chamber 130, where the $air_1(t+1)$ 376A may be generated by the air quality controller 320 to have lower level of carbon dioxide.

In some embodiments, the air quality controller 320 and the non-airflow control assembly 350 may control environment conditions in the manipulation chamber 120, the incubator culture chamber 130, the inlet chamber 140, the outlet chamber 150, and/or the accessory chamber 160 further based on the thermal control signals 368. As will be described with respect to FIG. 4, the thermal control signals 368 may be generated by the intelligent manipulator subsystem 104 based on real-time object information (e.g., identity and location of an object) and thermal imaging data (e.g., temperature of the object). In some embodiments, the thermal control signals 368 may cause the air quality controller 320 to generate warmer or cooler air to flow through the airflow assembly 340C to the manipulation chamber 120 when the real-time object information and the thermal imaging data show that temperature of liquid within a pipette that is held by the manipulator assembly 450 above the working table 460 in the manipulation chamber 120 deviates from a desired temperature.

In other embodiments, the thermal control signals 368 may cause the non-airflow control assembly 350 to activate a heater 354 that is on or around a spot of the working table 460 when the real-time object information and the thermal imaging data show that temperature inside a Petri dish or a culture vessel that holds biological samples placed on the spot of the working table 460 deviates from a desired temperature. In these two examples, the amount of temperature adjustment may depend on the identities of biological samples inside the culture vessel. For example, when the culture vessel placed on the working table 460 holds an embryo for IVF treatments, the thermal control signals 368 may cause the heater 354 to heat the culture vessel toward 37° C. Advantageously, by using both the non-airflow control assembly 350 that is controlled by the thermal control signals 368 and the quality control assembly 324 (e.g., air filters 330, air reservoir 326, and/or air heater 328) that is connected to the airflow assemblies 340A-340N to control environment conditions at particular chambers and/or particular spots in a chamber, the automatic incubator system 100 can more efficiently (e.g., within less amount of time) and accurately control air composition, humidity, and/or temperature within the case 230.

Figure 3B:
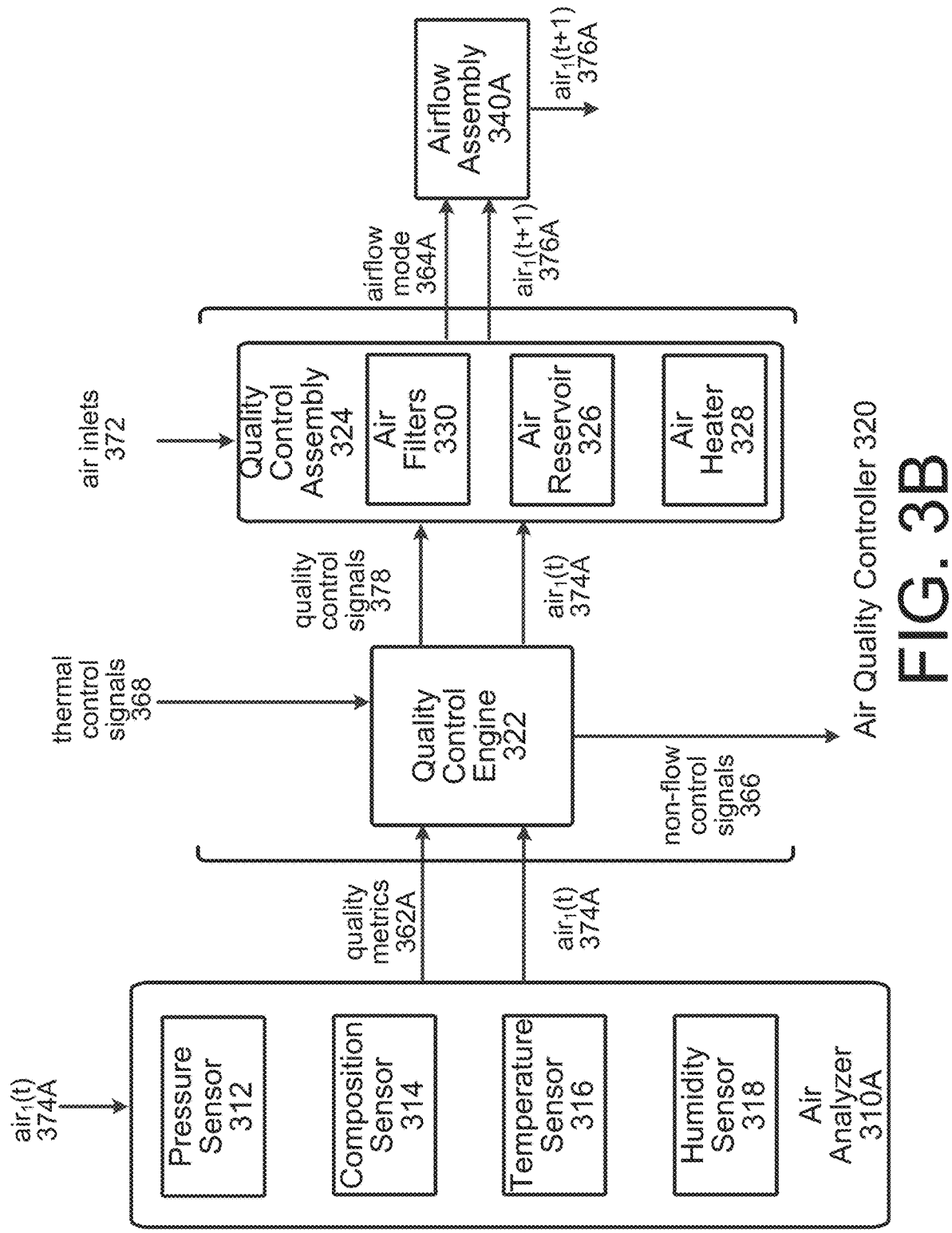
FIG. 3B is a block diagram illustrating a portion of the environment control subsystem of FIG. 3A in accordance with some embodiments of the present disclosure.

FIG. 3B is a block diagram illustrating a portion of the environment control subsystem 102 of FIG. 3A in accordance with some embodiments of the present disclosure. As illustrated in FIG. 3B, the air analyzer 310A includes a pressure sensor 312, a composition sensor 314, a temperature sensor 316, and a humidity sensor 318. The air quality controller 320 includes a quality control engine 322, and a quality control assembly 324. The pressure sensor 312, the composition sensor 314, the temperature sensor 316, and the humidity sensor 318 of the air analyzer 310A may sense and analyze the $air_1(t)$ 374A from the incubator culture chamber 130 to generate quality metrics 362A that indicate air quality in the incubator culture chamber 130.

The quality control engine 322 may be a combination of hardware, firmware, and software. The quality control engine 322 may set or determine the airflow modes 364A through 364N. Based at least on the quality metrics 362A and the thermal control signals 368, the quality control engine 322 may generate the non-flow control signals 366 to the non-airflow control assembly 350 for controlling environment conditions within the incubator culture chamber 130 through adjusting air composition (e.g., using the air absorbers 352) or temperature (e.g., using the heater 354). Based at least on the quality metrics 362A and the thermal control signals 368, the quality control engine 322 may generate the quality control signals 378 to control the quality control assembly 324 for generating the $air_1(t+1)$ 376A using the air inlets 372 and the $air_1(t)$ 374A.

The quality control assembly 324 may include the air reservoir 326, the air heater 328, and the air filters 330. The air filters 330 may include volatile organic compounds (VOC) filter, high-efficiency particulate air (HEPA) filter, or other types of filters that can filter air within the automatic incubator system 100. Although not illustrated in FIG. 3B, the quality control assembly 324 may include other air quality control equipment, such as a humidifier. The quality control signals 378 may indicate to the quality control assembly 324 the percentage of the air inlets 372 that is to be used and the $air_1(t)$ 374A that is to be processed (e.g., circulated and filtered) by the quality control assembly 324 to generate the $air_1(t+1)$ 376A for the incubator culture chamber 130. The quality control signals 378 may cause the quality control assembly 324 to generate the $air_1(t+1)$ 376A to flow to the incubator culture chamber 130 through the airflow assembly 340A to maintain air quality in the incubator culture chamber 130 at a desired condition. In some embodiments, depending on the stages of cell culture, the quality control engine 322 may generate the quality control signals 378 to adjust the desired condition at a particular chamber.

In some embodiments, when the quality control engine 322 determines that changes of air composition exceed a particular threshold based on the quality metrics 362A, the quality control engine 322 may utilize the air reservoir 326 to quickly restore air composition. For example, when the quality metrics 362A indicates that nitrogen level in the incubator culture chamber 130 suddenly increases by certain percentage (e.g., 6%) beyond a desired level (e.g., 89%) due to release of liquid nitrogen associated with automated cryopreservation, the quality control engine 322 may generate the quality control signals 378 to cause the air reservoir 326 to flush air having less nitrogen composition to the incubator culture chamber 130. As such, nitrogen level within the incubator culture chamber 130 may be immediately reduced to the desired level. In this example, the quality control signals 378 may also activate the air heater 328 to cause air having higher temperature flowing to the chamber where the liquid nitrogen is released toward. Additionally, the thermal control signals 368 may cause the quality control engine 322 to generate the non-flow control signals 366 to activate a heater 354 to increase temperature around a spot that the liquid nitrogen is released toward.

In some embodiments, when the quality control engine 322 determines based on the quality metrics 362A that temperature within the incubator culture chamber 130 is lower than a desired temperature, the quality control engine 322 may generate the quality control signals 378 to trigger the air heater 328 to generate the $air_1(t+1)$ 376A that is heated toward or beyond the desired temperature to flow through the airflow assembly 340A to the incubator culture chamber 130. Advantageously, the air heater 328 and the heaters 354 can adjust temperature within a particular chamber or around a particular spot within a chamber respectively through airflow control mechanisms and non-airflow control mechanisms.

In some embodiments, when the quality control engine 322 determines based on the quality metrics 362N that temperature at certain spots on the working table 460 in the manipulation chamber 120 is lower than a desired temperature, the quality control engine 322 may generate the quality control signals 378 to trigger the air heater 328 to generate the $air_n(t+1)$ 376N. The $air_n(t+1)$ 376N may be heated toward or beyond the desired temperature and may flow through the airflow assembly 340N to the certain spots on the working table 460 in the manipulation chamber 120. As noted above, the air heater 328 and the heaters 354 can advantageously adjust temperature within a particular chamber or around a particular spot within a chamber respectively through airflow control mechanisms and non-airflow control mechanisms.

Example Intelligent Manipulator Subsystem

Figure 4:
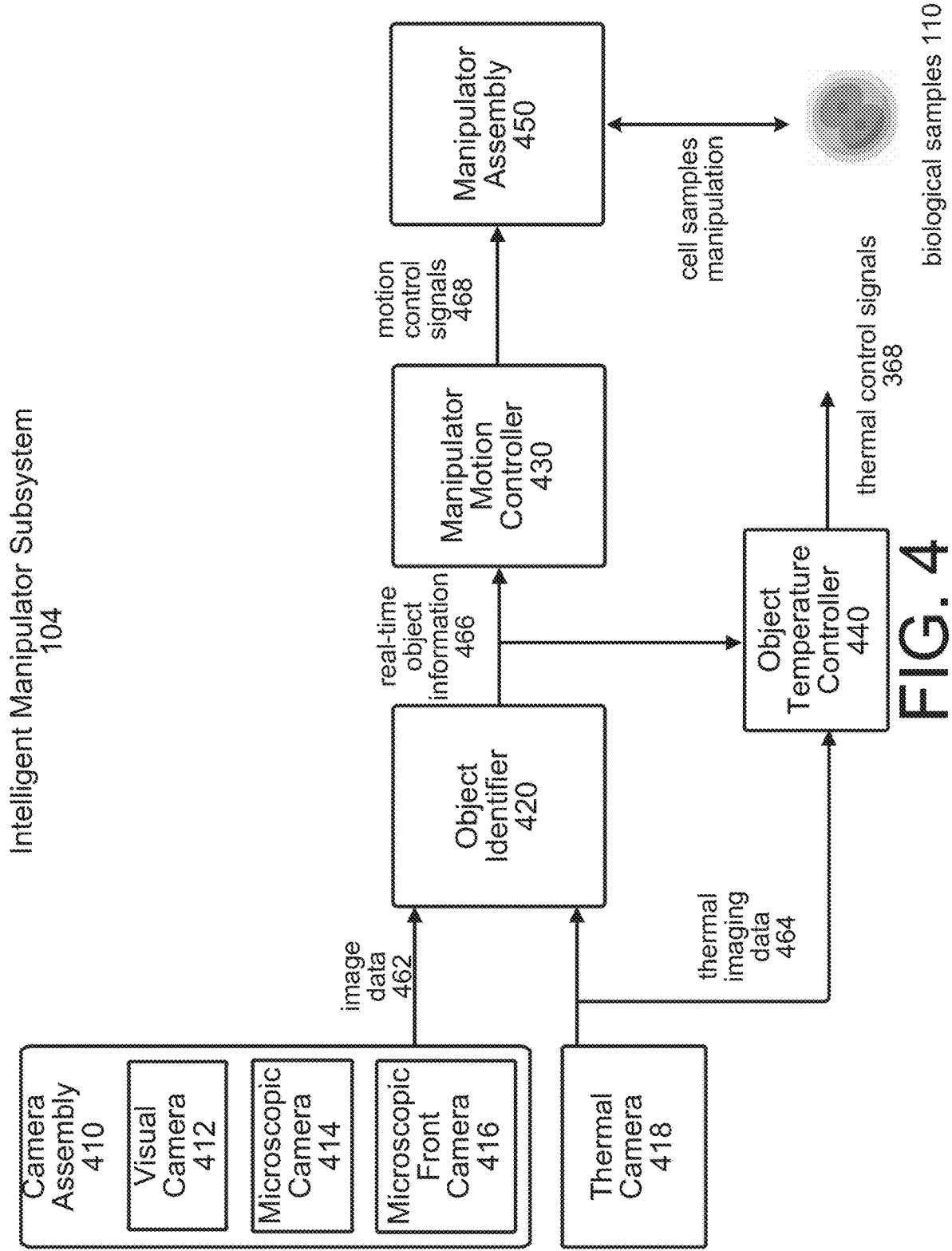
FIG. 4 is a block diagram illustrating the intelligent manipulator system of FIG. 1 in accordance with some embodiments of the present disclosure.

FIG. 4 is a block diagram illustrating the intelligent manipulator subsystem 104 of FIG. 1 in accordance with some embodiments of the present disclosure. As illustrated in FIG. 4, the intelligent manipulator subsystem 104 includes the camera assembly 410, the thermal camera 418, the object identifier 420, the manipulator motion controller 430, the object temperature controller 440, and the manipulator assembly 450. The camera assembly 410 includes the visual camera 412, the microscopic camera 414, and the microscopic front camera 416.

As illustrated in FIG. 4, based on image data 462 generated by the camera assembly 410 and thermal imaging data 464 generated by the thermal camera 418, the object identifier 420 may generate real-time object information 466. The image data 462 may depict images associated with objects inside the automatic incubator system 100. The thermal imaging data 464 may include thermal information associated with the objects. The real-time object information 466 may include at least identities (e.g., an oocyte, an embryo, a culture vessel, a pipette, or the like) and locations (e.g., a position in a coordinate defined by the automatic incubator system 100) of objects that are to be manipulated by the manipulator assembly 450.

Based on the real-time object information 466 and the thermal imaging data 464, the object temperature controller 440 may generate thermal control signals 368 that are to be utilized by the air quality controller 320 and the non-airflow control assembly 350 for controlling environment conditions within the automatic incubator system 100 as described with respect to FIGS. 3A and 3B. The thermal control signals 368 may cause the air quality controller 320 to flow air having certain temperature to a particular chamber or cause a heater 354 at a particular spot in the particular chamber to be activated for controlling environment conditions within one or more particular areas and culture vessels. Based on the real-time object information 466, the manipulator motion controller 430 may generate the motion control signals 468 to control the manipulator assembly 450 to manipulate biological samples 110. Advantageously, by utilizing the thermal control signals 368 and quality metrics 362A-362N to control the air quality controller 320 and the non-airflow control assembly 350 for adjusting environment conditions within the manipulation chamber 120 and incubator culture chamber 130, the automatic incubator system 100 can more quickly and accurately keep environment conditions within the manipulation chamber 120 and incubator culture chamber 130 under target condition(s).

As noted above, the visual camera 412 and the thermal camera 418 may be installed around a ceiling (e.g., attached to the case 230) of the automatic incubator system 100 to widely monitor areas or spots within the manipulation chamber 120, the incubator culture chamber 130, the inlet chamber 140, the outlet chamber 150, and/or the accessory chamber 160. The microscopic camera 414 and the microscopic front camera 416 may be installed on or integrated with the manipulator assembly 450. In some embodiments, the visual camera 412 may be a charge-coupled device camera, a digital single-lens reflex (DSLR) camera, a video camera, a 3D camera, or any other suitable types of cameras that can generate a portion of the image data 462 for obtaining positions of objects to control macro-movement (e.g., moving in a distance scale in an order of a centi-meter, transporting biological samples 110 from the manipulation chamber 120 to the incubator culture chamber 130, or the like) of the manipulator assembly 450.

In some embodiments, the microscopic camera 414 may be a bright-field microscope, a phase-contrast microscope, a polarized microscope, an inverted microscope, a Shmidt objective microscope, an optical microscope, or any other types of microscope cameras that can generate a portion of the image data 462 for controlling fine-movement (e.g., moving in a distance scale in or smaller than an order of a milli-meter, positioning the biological samples 110 for observation by the microscopic front camera 416, loading and unloading the biological samples 110) of the manipulator assembly 450. The microscopic camera 414 may have a magnification factor up to 500×, 750×, 1000×, 1500×, 2000×, or any other ranges of values therebetween.

In some embodiments, the microscopic front camera 416 may be an electron microscope or any other types of microscopes that can generate a portion of the image data 462 for controlling the manipulator assembly 450 to micro-manipulate (e.g., holding a pipette that includes the biological samples 110 such as embryos, aspirating a mammalian oocyte, injecting a sperm into an unfertilized egg, or the like) the biological samples 110. The microscopic front camera 416 may have a magnification factor above 1000× and up to 10,000,000×, or any other ranges of values therebetween.

In some embodiments, the thermal camera 418 may be a cool infrared camera, an uncooled infrared camera, a long-wave infrared (LWIR) camera, a medium-wave infrared (MWIR) camera, a short-wave infrared (SWIR) camera, or other types of thermographic cameras that can generate thermal imaging data 464 through detecting energy (e.g., infrared energy or heat) for visual image conversion to depict spatial distribution of temperature differences in the automatic incubator system 100.

Based on image data 462 and thermal imaging data 464, the object identifier 420 may generate real-time object information 466. More specifically, the object identifier 420 may include a feature engine and/or a machine learning model. The feature engine may analyze the image data 462 and/or the thermal imaging data 464 to extract features (e.g., shape features) associated with objects that are to be manipulated by the manipulator assembly 450. Based on the extracted features, the machine learning model may generate the real-time object information 466 that identifies and positions the objects for manipulation. In some examples, the object identifier 420 may include the machine learning model without the feature engine. In these examples, the machine learning model may process the image data 462 and/or the thermal imaging data 464 (e.g., for extracting features) and generate the real-time object information 466 (e.g., via a forward pass through the model). In some embodiments, the machine learning model may be a support vector machine ("SVM"), a deep learning model, a recurrent neural network ("RNN"), or any other suitable artificial intelligence ("AI") models. The machine learning model may be trained for applications related to manipulating culture vessels, laboratory equipment, and/or micro-manipulate oocytes, embryos, ovums, sperms, organoid, cells, or tissues.

Figure 5A:
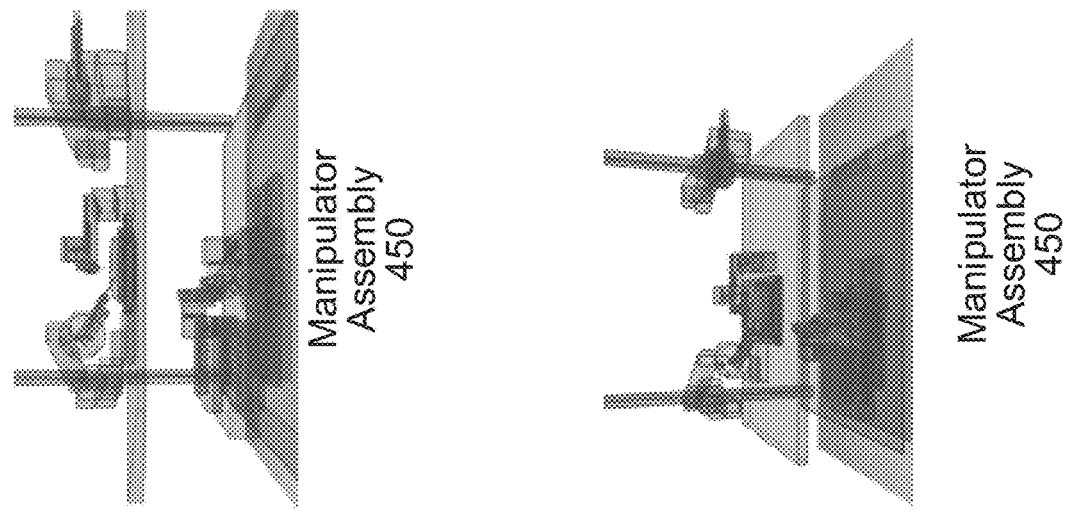
FIG. 5A illustrates an example enlarged perspective view of a portion of the intelligent manipulator system of FIG. 1 in accordance with some embodiments of the present disclosure.
Figure 5A:
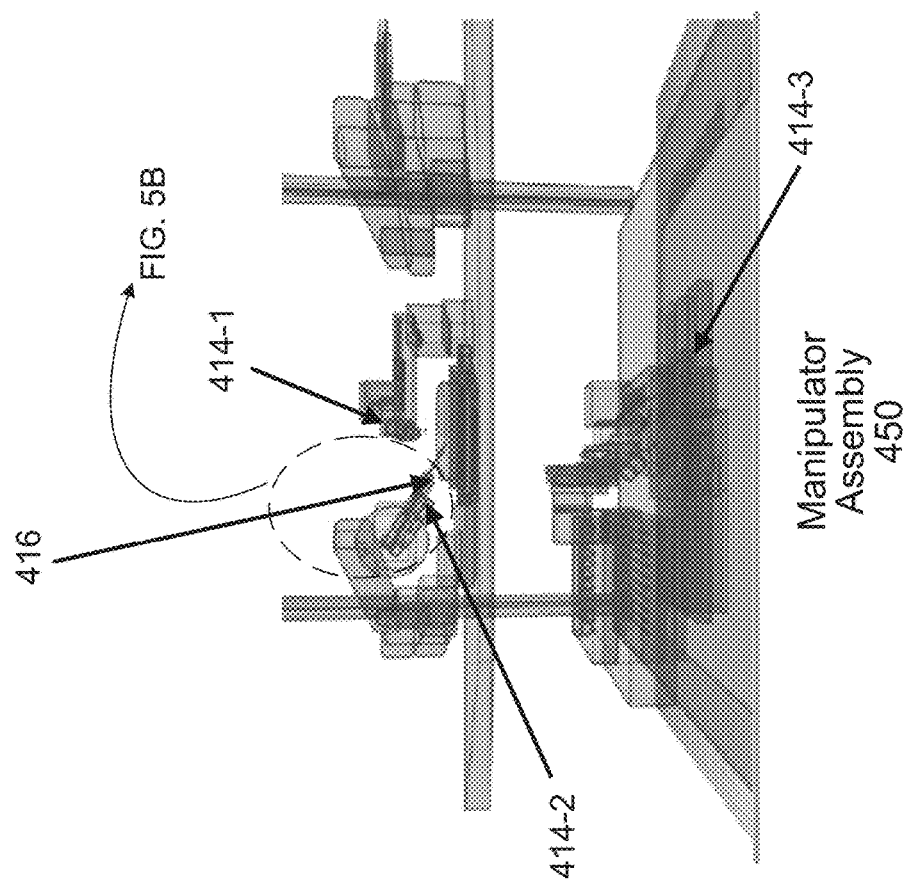

FIG. 5A illustrates example perspective views from various angles of a portion (e.g., the microscopic cameras 414-1, 414-2, and 414-3, the microscopic front camera 416, and the manipulator assembly 450) of the intelligent manipulator subsystem 104 of FIG. 1 in accordance with some embodiments of the present disclosure. As illustrated in FIG. 5A, the microscopic cameras 414 and the microscopic front camera 416 are integrated with the manipulator assembly 450. In some embodiments, the microscopic camera 414-1 is a standing microscope, 414-2 is a mobile manipulator-integrated microscope, and 414-3 is a polarized inverted microscope.

Figure 5B:
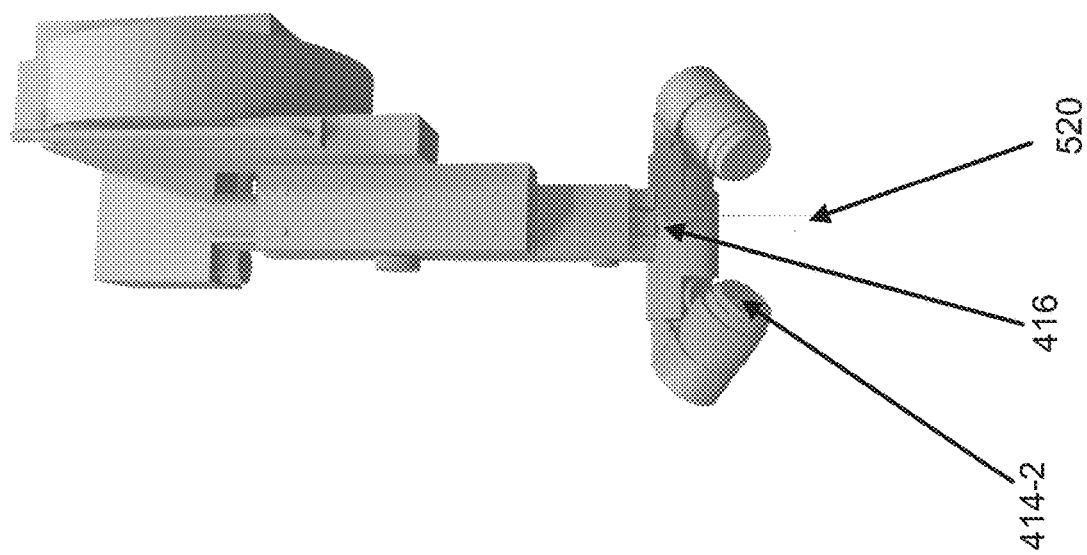
FIG. 5B illustrates an enlarged representation of a portion of the example perspective view of FIG. 5A in accordance with some embodiments of the present disclosure.
Figure 5B:
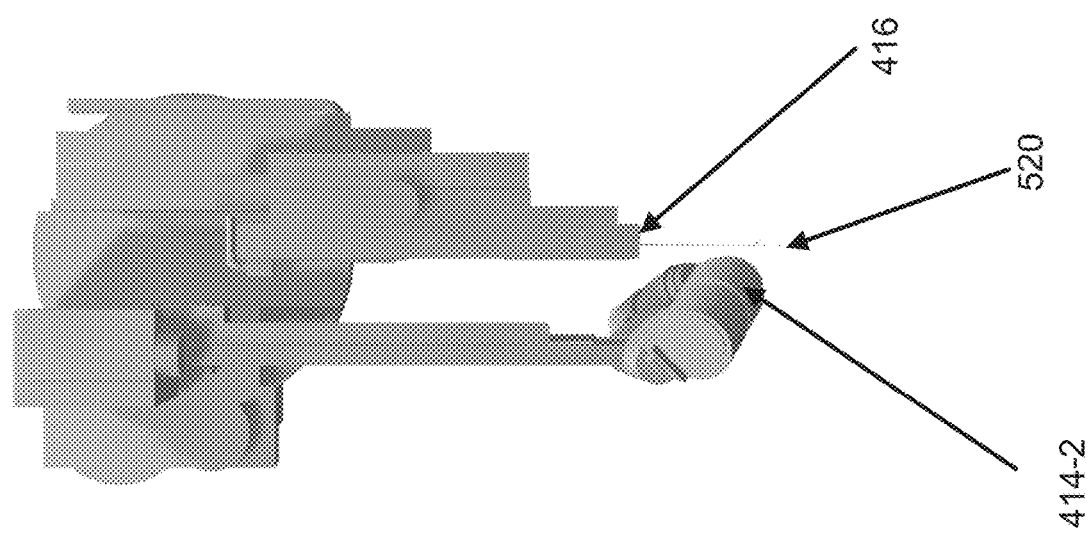

FIG. 5B illustrates an enlarged representation of the portion of the intelligent manipulator subsystem 104 illustrated in FIG. 5A in accordance with some embodiments of the present disclosure. As illustrated in FIG. 5B, the microscopic camera 414-2 is attached to a part of the manipulator assembly 450. The microscopic front camera 416 is installed adjacent to a cell picker 520. The cell picker 520 may detect, pick, prick, pressure, contact, probe, or otherwise manipulate the biological samples 110 through the aid of microscopic front camera 416. In some embodiments, the cell picker 520 may be a ICSI needle, a biopsy needle, or a laser.

In some embodiments, the cell picker 520 and the microscopic front camera 416 may be directed toward the same direction (e.g., toward the same biological sample, not shown in FIG. 5B) to advantageously enable micro-manipulation on the biological sample. As noted above, by integrating the intelligent manipulator subsystem 104 (e.g., the manipulator assembly 450 that is motion controlled by machine learning model using image data 462 and thermal imaging data 464), the manipulation chamber 120, and the incubator culture chamber 130 within the case 230, the automatic incubator system 100 can implement streamlined and automated cell culture or laboratory procedures without involvement of human labor from professionals. As such, environment within the case 230 is less likely to fluctuate because of presence of human. With highly integrated and compact in size (e.g., the case having a volume smaller than 500 L) design, the automatic incubator system 100 may further advantageously allow unmanned or remote controlled for various applications (e.g., cell culture underwater or cell culture inside spacecraft).

Example Flowcharts

Figure 6A:
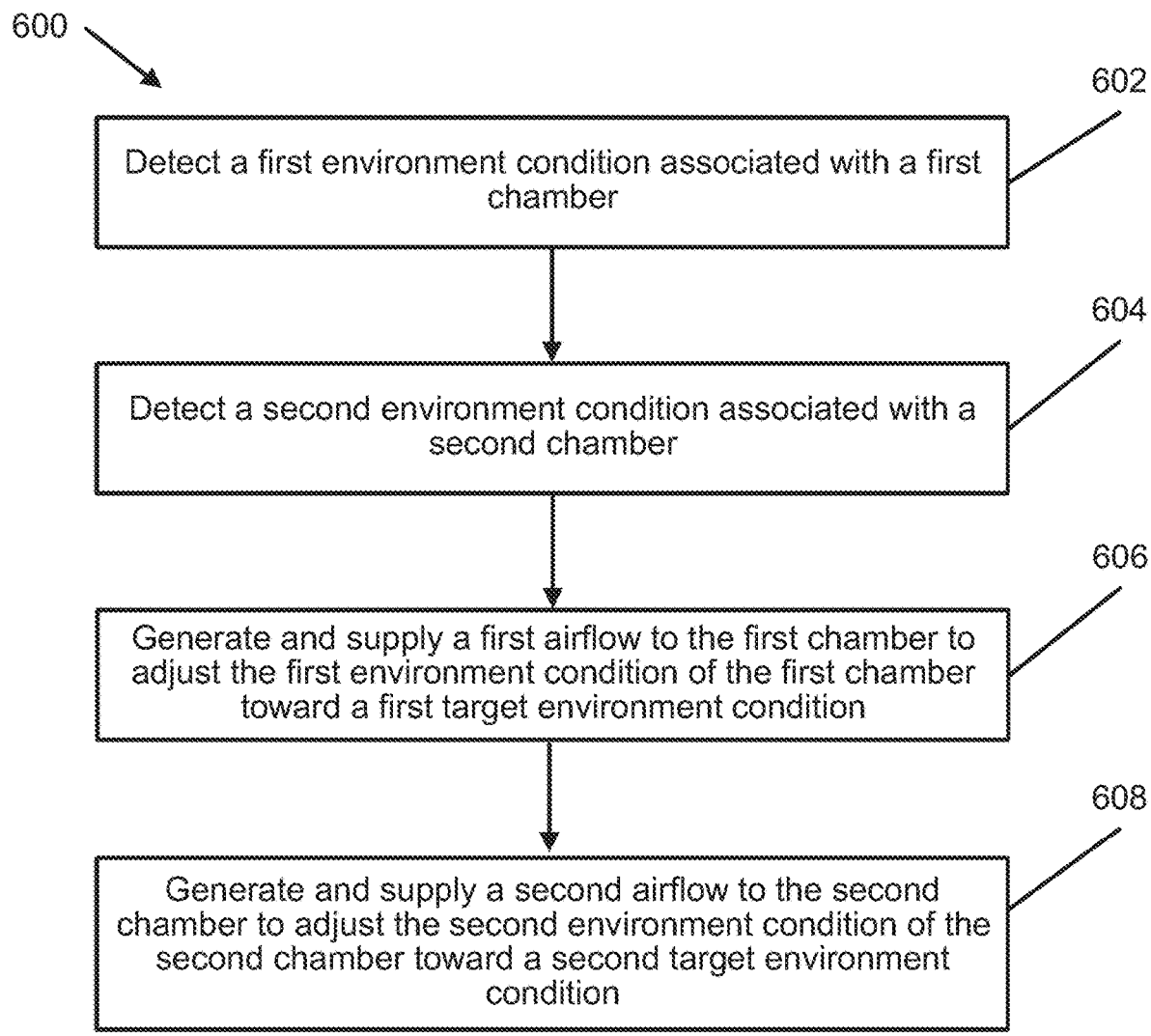
FIG. 6A is a flowchart for controlling environment conditions in the example automatic incubator system of FIG. 1 in accordance with some embodiments of the present disclosure.

FIG. 6A is a flowchart of an example process 600 for controlling environment conditions in an incubator system, such as the automatic incubator system 100 of FIG. 1, in accordance with some embodiments of the present disclosure. All or at least some parts of the process 600 may be implemented, for example, by the automatic incubator system 100 of FIG. 1. It should be noted that at least some parts of the process 600 may be performed concurrently, sequentially, or in different orders. The process 600 may provide for detecting environment conditions in various chambers (e.g., the manipulation chamber 120 and the incubator culture chamber 130) and utilizing the same or different airflow modes to respectively adjust environment conditions in the various chambers. As such, the process 600 may be utilized to achieve more effective, time-efficient, and accurate environment conditions control.

At block 602, the automatic incubator system 100 detects a first environment condition associated with a first chamber. For example, the air analyzer 310A may detect the environment condition in the incubator culture chamber 130. The environment condition may include temperature, humidity, pressure, and/or air composition in the incubator culture chamber 130.

At block 604, the automatic incubator system 100 detects a second environment condition associated with a second chamber. For example, an air analyzer 310B may detect the environment condition in the manipulation chamber 120. The environment condition may include temperature, humidity, pressure, and/or air composition in the manipulation chamber 120.

At block 606, the automatic incubator system 100 may generate and supply a first airflow to the first chamber to adjust the first environment condition of the first chamber toward a first target environment condition. For example, the air quality controller 320 may generate the first airflow to the incubator culture chamber 130 based on the environment condition of the incubator culture chamber 130, the first target environment condition, and a first airflow mode. As noted above, the first target environment condition may specify at least a target temperature, a target humidity, and a target air composition. For example, in the context of utilizing the automatic incubator system 100 for IVF treatments, the target temperature may be 37° C., the target humidity may be 40%, and the target air composition may include 5% oxygen, 6% carbon dioxide, and 89% nitrogen. The first airflow mode may be selected by a user through a user interface, or determined based on various factors (e.g., a cell culture activity that is conducted inside the first chamber, a size of the first chamber, and/or a remaining capacity of an air tank that supplies air to the first chamber) discussed above. As also noted above, the cell culture activity (e.g., culturing unknown cells, culturing cells that are toxic, culturing mammalian oocytes, manipulating mammalian oocytes, manipulating other biological samples, or the like) that is conducted inside the first chamber can be defined or specified through a user interface, or automatically determined by the intelligent manipulator subsystem 104.

In some embodiments, the first airflow mode may be one of the one-way airflow mode, semi-close airflow mode, and close airflow mode. When the first airflow mode is the one-way airflow mode, the air quality controller 320 may generate the first airflow based on air inlets 372 without circulating air inside the incubator culture chamber 130. When the first airflow mode is the close airflow mode, the air quality controller 320 may generate the first airflow by circulating air inside the incubator culture chamber 130 without using the air inlets 372. The airflow assembly 340A may supply (e.g., direct and guide) the first airflow to the incubator culture chamber 130 to adjust the first environment condition of the incubator culture chamber 130 toward the first target environment condition.

At block 608, the automatic incubator system 100 may generate and supply a second airflow to the second chamber to adjust the second environment condition of the second chamber toward a second target environment condition. The second target environment condition can be the same as or different from the first target environment condition. For example, the air quality controller 320 may generate the second airflow to the manipulation chamber 120 based on the environment condition of the manipulation chamber 120, the second target environment condition, and a second airflow mode. The airflow assembly 340B may supply (e.g., direct and guide) the second airflow to the manipulation chamber 120 to adjust the second environment condition of the manipulation chamber 120 toward the second target environment condition.

Figure 6B:
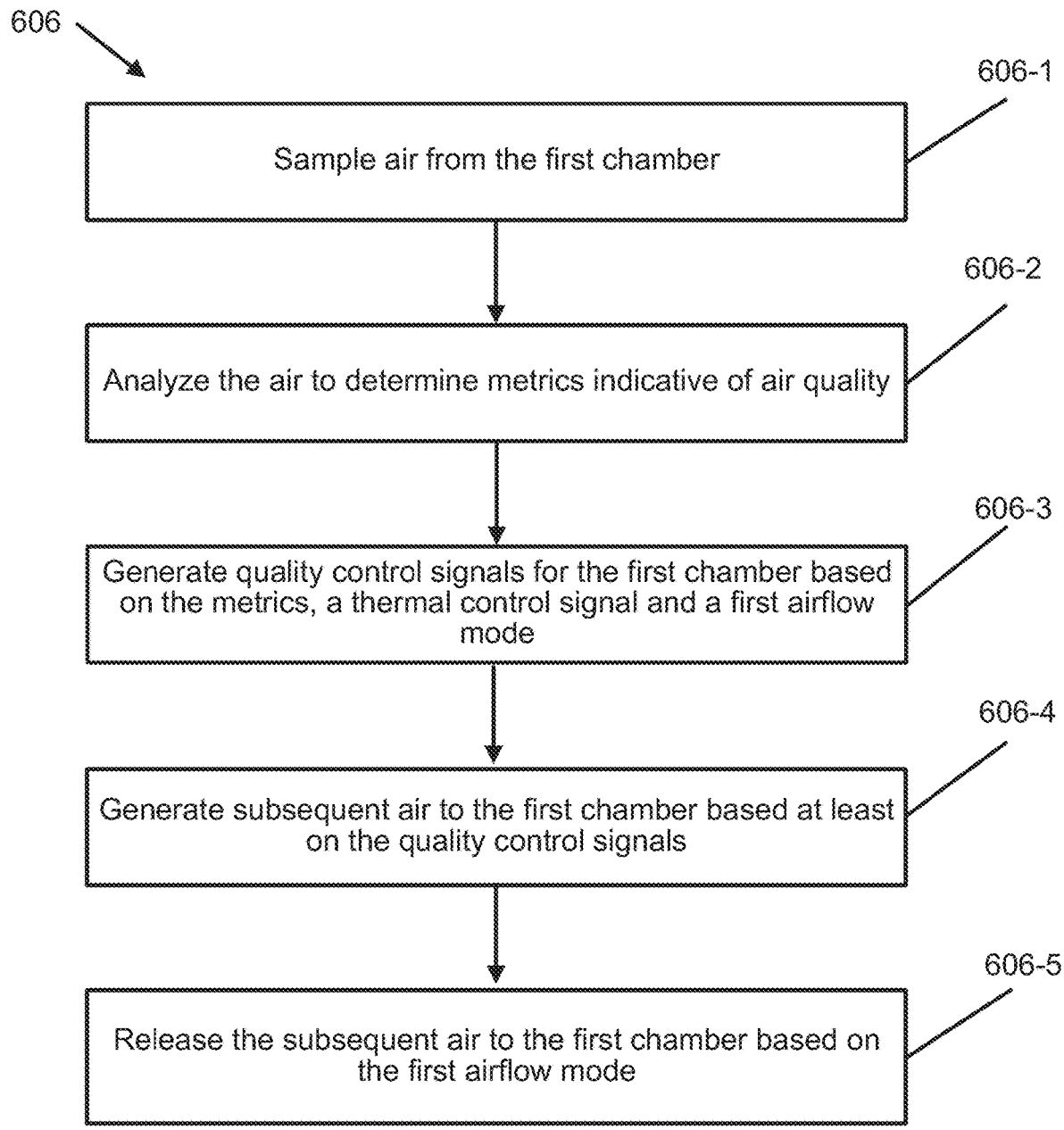
FIG. 6B is a flowchart of an example process for controlling air quality in the example automatic incubator system of FIG. 1 in accordance with some embodiments of the present disclosure.

FIG. 6B is a flowchart illustrating an example implementation of the block 606 (and/or the block 608) for controlling air quality in the example automatic incubator system of FIG. 1 in accordance with some embodiments of the present disclosure.

At block 606-1, the automatic incubator system 100 may sample air from the first chamber. For example, the airflow assembly 340A may sample and direct some air (e.g., the $air_1(t)$ 374A) inside the incubator culture chamber 130 to the housing 220 that houses the air analyzer 310A and the air quality controller 320.

At block 606-2, the automatic incubator system 100 may analyze the air to determine metrics indicative of air quality. For example, the air analyzer 310A may analyze the $air_1(t)$ 374A to determine the quality metrics 362A that indicate air quality (e.g., temperature, humidity, pressure, and/or air composition) of the air inside the incubator culture chamber 130.

At block 606-3, the automatic incubator system 100 may generate quality control signals for the first chamber based on the metrics, a thermal control signal, and a first airflow mode. For example, based on the quality metrics 362A, the thermal control signals 368, and the airflow mode 364A, the quality control engine 322 may generate the quality control signals 378 to control the quality control assembly 324. More specifically, when the quality metrics 362A indicates that temperature within the incubator culture chamber 130 is lower than a target temperature, the quality control engine 322 may generate the quality control signals 378 to cause the air heater 328 to generate the $air_1(t+1)$ 376A having higher temperature than the $air_1(t)$ 374A. As another example, when the thermal control signals 368 indicates that temperature at a particular spot of the incubator culture chamber 130 is lower than the target temperature, the quality control engine 322 may generate the quality control signals 378 to cause the quality control assembly 324 and the airflow assembly 340A to flow warmer air (e.g., $air_1(t+1)$ 376A) to the particular spot of the incubator culture chamber 130.

At block 606-4, the automatic incubator system 100 may generate subsequent air to the first chamber based at least on the quality control signals. For example, the quality control assembly 324 may generate the $air_1(t+1)$ 376A based on the quality control signals 378. More specifically, the quality control signals 378 may cause the quality control assembly 324 to generate $air_1(t+1)$ 376A by circulating and filtering air (e.g., $air_1(t)$ 374A) from the incubator culture chamber 130 when the airflow mode 364A is the semi-close airflow mode or the close airflow mode. The quality control signals 378 may cause the quality control assembly 324 to generate $air_1(t+1)$ 376A using the air inlets 372 without circulating air inside the incubator culture chamber 130 when the airflow mode 364A is the one-way airflow mode.

At block 606-5, the automatic incubator system 100 may release the subsequent air to the first chamber based on the first airflow mode. For example, the airflow assembly 340A may direct and guide the $air_1(t+1)$ 376A to the incubator culture chamber 130 based on the airflow mode for the incubator culture chamber 130. More specifically, when the airflow mode 364A is the close airflow mode, the airflow assembly 340A may cause the $air_1(t+1)$ 376A to flow to the incubator culture chamber 130 at a lower frequency (e.g., under lower TACH and FACH) compared with the situation when the airflow mode 364A is the semi-close airflow mode.

Figure 7A:
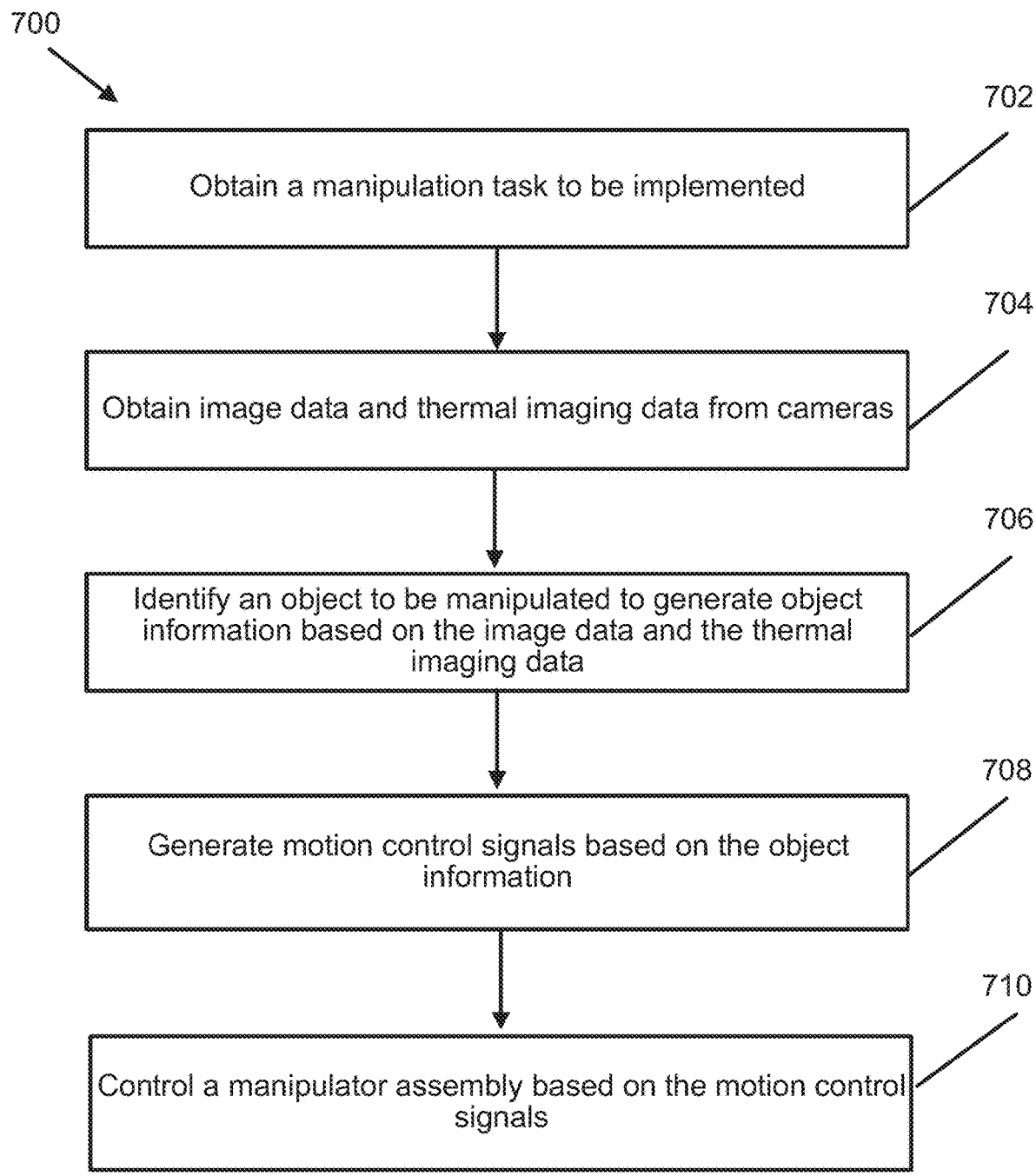
FIGS. 7A-7B are flowcharts of an example processes for controlling a manipulator assembly to manipulate biological samples in accordance with some embodiments of the present disclosure.

FIG. 7A is a flowchart of an example process 700 for controlling a manipulator assembly, such as the manipulator assembly 450, to manipulate the biological samples 110 in accordance with some embodiments of the present disclosure. All or at least some parts of the process 700 may be implemented, for example, by the intelligent manipulator subsystem 104 of FIG. 1. The process 700 may provide for automatically manipulating the biological samples 110 without resorting to human labor from professionals (e.g., embryologists).

At block 702, the automatic incubator system 100 obtains a manipulation task to be implemented. For example, the intelligent manipulator subsystem 104 may obtain the manipulation task to be implemented from a user through a user interface (e.g., a user interface 800 that will be described in FIG. 8). The manipulation task may include transporting the biological samples 110 from the inlet chamber 140 to the incubator culture chamber 130, loading and unloading the biological samples 110, positioning the biological samples 110, holding a pipette that includes the biological samples 110, injecting a sperm into an unfertilized egg, and injecting a sperm into an unfertilized egg under the guidance, control, and observation of the microscopic cameras 414-1, 414-2, and/or 414-3 and the microscopic front camera 416, or the like. As noted above, in some embodiments, the microscopic camera 414-1 is a standing microscope, the microscopic camera 414-2 is a mobile manipulator-integrated microscope, and the microscopic camera 414-3 is a polarized inverted microscope.

At block 704, the automatic incubator system 100 obtains image data and thermal imaging data from cameras. For example, the object identifier 420 of the intelligent manipulator subsystem 104 obtains the image data 462 generated by the camera assembly 410 and the thermal imaging data 464 generated by the thermal camera 418.

At block 706, the automatic incubator system 100 identifies an object to be manipulated to generate object information based on the image data and the thermal imaging data. For example, the object identifier 420 generates the real-time object information 466 based on the image data 462 and the thermal imaging data 464. The real-time object information 466 may identify the object that is to be manipulated. The real-time object information 466 may include identity (e.g., an oocyte, an embryo, a culture vessel, a pipette, or the like), temperature, and position information (e.g., a position in a coordinate defined by the automatic incubator system 100) associated with the object that is to be manipulated by the manipulator assembly 450.

At block 708, the automatic incubator system 100 generates motion control signals based on the object information. For example, the manipulator motion controller 430 may generate the motion control signals 468 based on the real-time object information 466.

At block 710, the automatic incubator system 100 controls a manipulator assembly based on the motion control signals. For example, the manipulator motion controller 430 controls the manipulator assembly 450 to manipulate the biological samples 110 based on the motion control signals 468 generated at block 708.

Figure 7B:
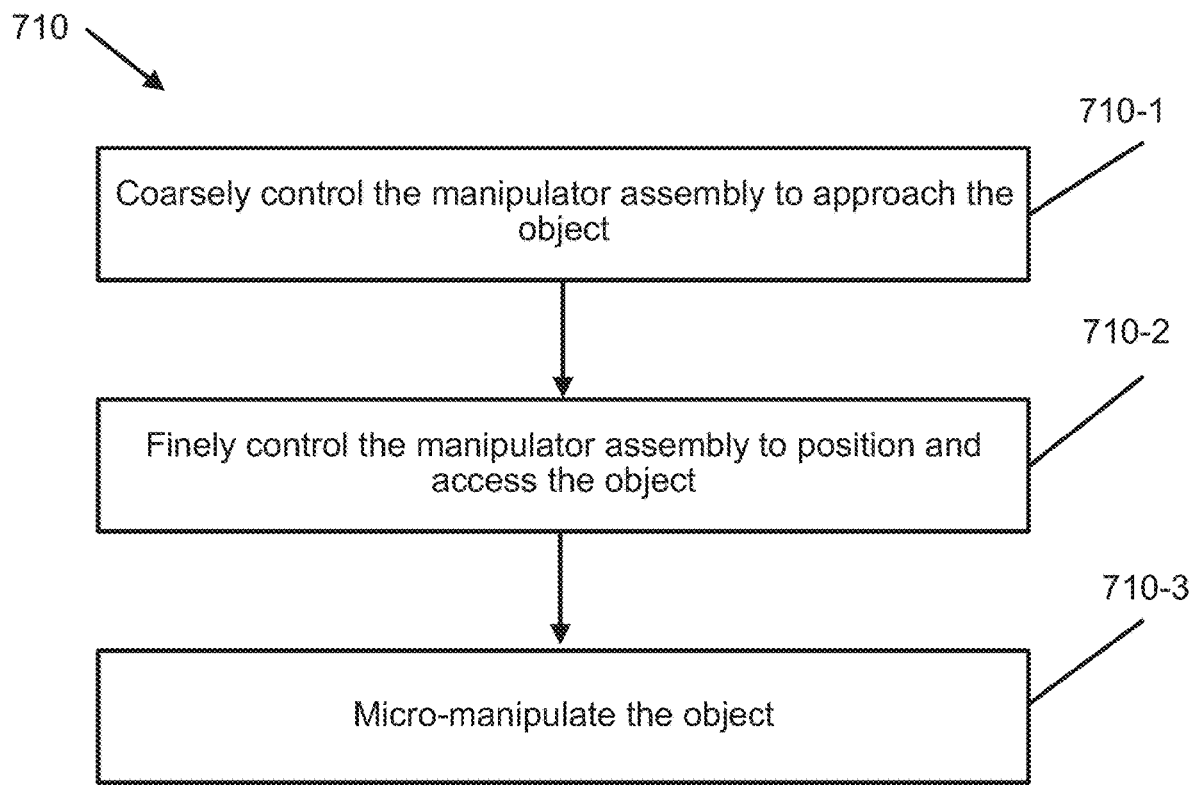

FIG. 7B is a flowchart illustrating an example implementation of the block 710 for controlling the manipulator assembly to manipulate the biological samples 110. It should be noted that blocks 710-1, 710-2, and 710-3 may be performed concurrently, sequentially, iteratively, or in various orders.

At block 710-1, the automatic incubator system 100 coarsely controls the manipulator assembly to approach the object. For example, based on a portion of the image data 462 generated by the visual camera 412, the manipulator motion controller 430 may generate the motion control signals 468 to control macro-movement (e.g., moving in a distance scale in an order of a centi-meter to transport biological samples 110 from the incubator culture chamber 130 to the manipulation chamber 120 for manipulation) of the manipulator assembly 450.

At block 710-2, the automatic incubator system 100 finely controls the manipulator assembly to position and access the object. For example, based on a portion of the image data 462 generated by the microscopic camera 414 (e.g., the microscopic camera 414-1, the microscopic camera 414-2, the microscopic camera 414-3), the manipulator motion controller 430 may generate the motion control signals 468 to control fine-movement (e.g., moving in a distance scale in or smaller than an order of a milli-meter to position the biological samples 110 for observation by the microscopic front camera 416) of the manipulator assembly 450.

At block 710-3, the automatic incubator system 100 micro-manipulates the object. For example, based on a portion of the image data 462 generated by the microscopic front camera 416 and the microscopic camera 414, the manipulator motion controller 430 may generate the motion control signals 468 to control the manipulator assembly 450 to micro-manipulate (e.g., aspirate) the biological samples 110.

Example User Interfaces

Figure 8:
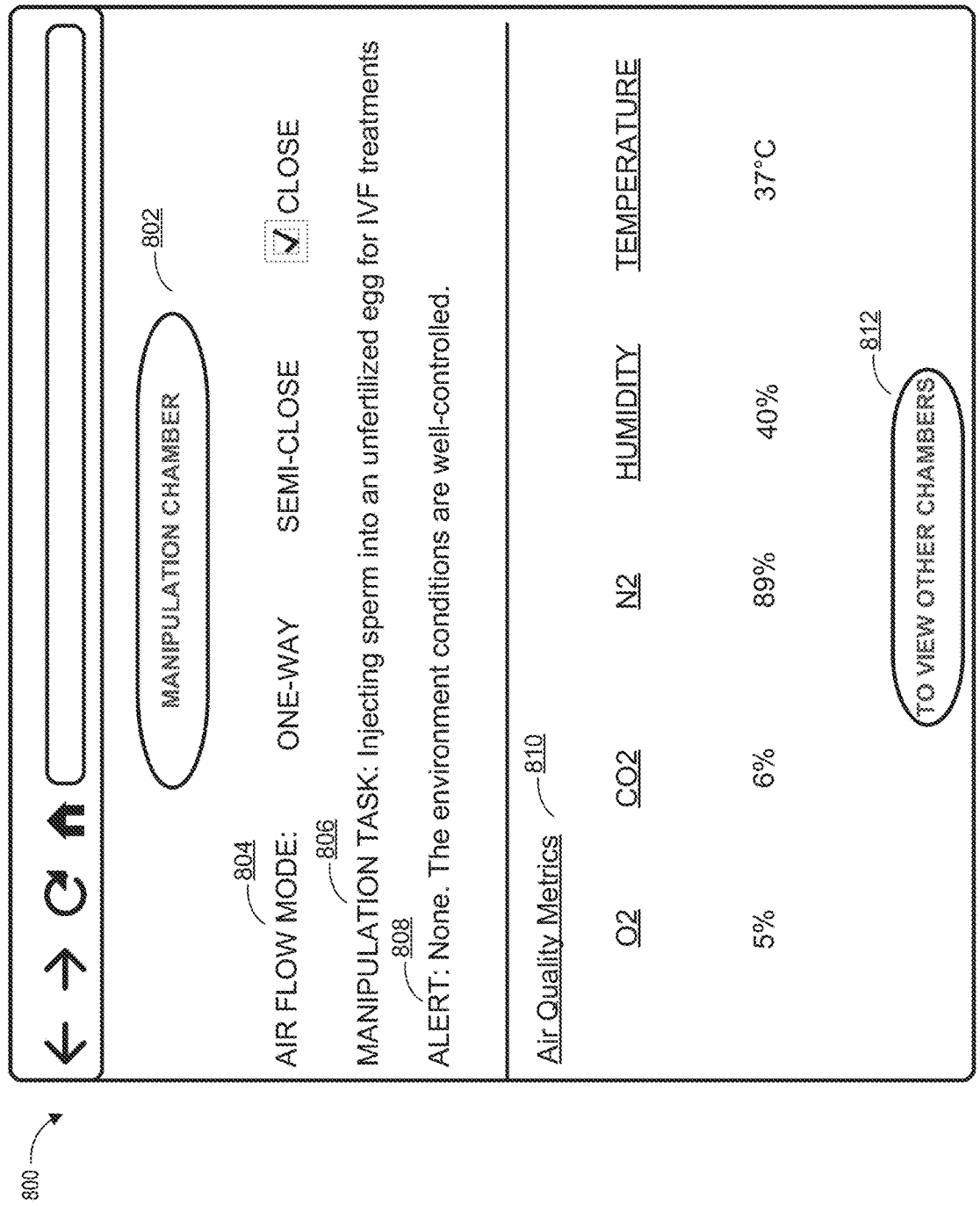
FIG. 8 illustrates an example user interface through which the example automatic incubator system can be monitored in accordance with some embodiments of the present disclosure.

FIG. 8 illustrates an example user interface 800 that allows a user to control and/or monitor the automatic incubator system 100 of FIG. 1. As shown in FIG. 8, the portion 802 indicates that the user interface 800 is displaying information about a manipulation chamber (e.g. the manipulation chamber 120). The portion 804 shows that the environment control subsystem 102 is controlling air quality inside the manipulation chamber 120 using the close airflow mode. The portion 806 shows the manipulation task that is performed by the manipulator assembly 450 inside the manipulation chamber 120. In some embodiments, the portion 806 allows a user to specify a cell culture activity that is conducted inside the manipulation chamber 120. The portion 806 may also allow the user to specify a cell culture activity that is to be conducted inside another chamber (e.g., the incubator culture chamber 130) when the portion 802 is switched from the "MANIPULATION CHAMBER" to "INCUBATOR CULTURE CHAMBER." As noted above, based on a cell culture activity specified by the user for being conducted in a particular chamber, the environment control subsystem 102 may determine an airflow mode (e.g., close airflow mode, one-way airflow mode, and semi-close airflow mode) for the particular chamber to supply an airflow to the particular chamber to adjust environment condition. Here, the portion 806 reads that the manipulation task that is performed is "injecting sperm into an unfertilized egg for IVF treatments." The portion 808 shows message to alert a user about environment conditions within the manipulation chamber 120. Here, the portion 808 reads "None. The environment conditions are well-controlled."

The portion 810 shows environment conditions within the automatic incubator system 100. More specifically, the portion 810 shows air quality within the manipulation chamber 120. Here, the portion 810 shows that the air composition within the manipulation chamber 120 includes 5% oxygen, 6% carbon dioxide, and 89% nitrogen. Further the portion 810 shows that, within the manipulation chamber 120, the humidity is 40% and the temperature is 37° C. The portion 812 allows the user to navigate to monitor and/or control environment conditions in other chambers of the automatic incubator system 100. Here, the portion 812 reads "to view other chambers." In some embodiments, the automatic incubator system 100 (e.g., the environment control subsystem 102) may control humidity within the manipulation chamber 120 and/or the incubator culture chamber 130 to be about 35%, 36%, 37%, 38%, 39%, 40%, 41%, 42%, 43%, 44%, 45%, or any range of values therebetween. In some embodiments, the automatic incubator system 100 (e.g., the environment control subsystem 102) may control the nitrogen level within the manipulation chamber 120 and/or the incubator culture chamber 130 to be about 35%, 85%, 86%, 87%, 89%, 90%, 91%, 92%, 93%, 94%, or any range of values therebetween.

Example System

Figure 9:
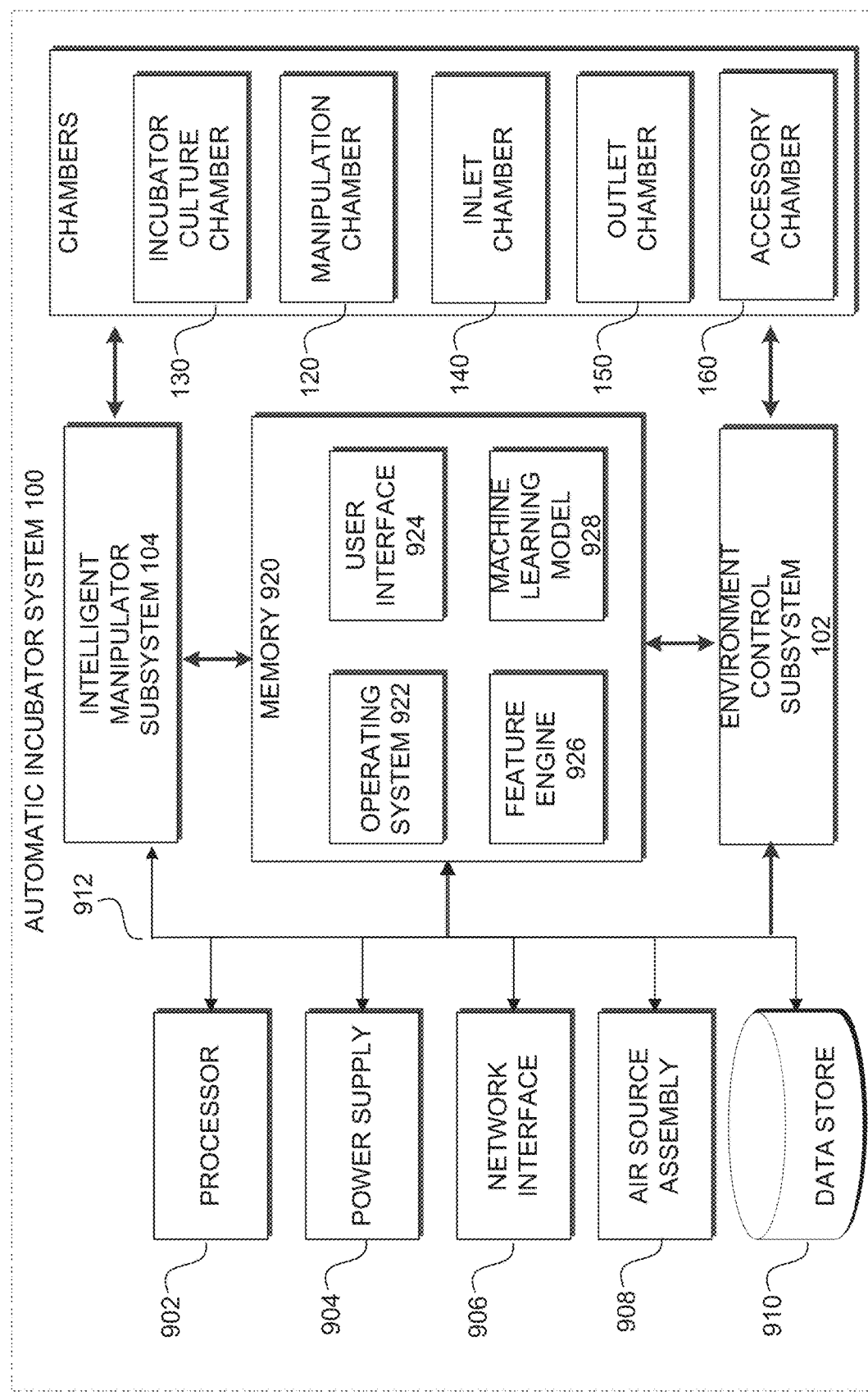
FIG. 9 illustrates a general architecture of an example automatic incubator system in accordance with some embodiments of the present disclosure.

FIG. 9 depicts a general architecture of an example system. The system may be used, in some embodiments to perform the functionality described herein. In some embodiments, the system may be the automatic incubator system 100, which includes an arrangement of computer hardware and software configured to implement aspects of the present disclosure. The automatic incubator system 100 may include more (or fewer) elements than those shown in FIG. 9. It is not necessary, however, that all of these elements be shown in order to provide an enabling disclosure.

As illustrated, the automatic incubator system 100 includes a processor 902, a power supply 904, a network interface 906, air source assembly 908, a data store 910, the intelligent manipulator subsystem 104, and the environment control subsystem 102, all of which may communicate with one another by way of a communication bus 912. The intelligent manipulator subsystem 104 may be configured to access each of the manipulation chamber 120, incubator culture chamber 130, inlet chamber 140, outlet chamber 150, and/or accessory chamber 160. The environment control subsystem 102 may be configured to control environment conditions within each of the manipulation chamber 120, incubator culture chamber 130, inlet chamber 140, outlet chamber 150, and/or accessory chamber 160.

The network interface 906 may provide connectivity to one or more networks or computing systems and, as a result, may enable the automatic incubator system 100 to receive and send information and instructions from and to other computing systems, interfaces (such as the user interface 800 of FIG. 8) or services. In some embodiments, the automatic incubator system 100 may be configured to process requests from other devices or modules, such as requests to adjust environment conditions toward a desired condition specified by a user. The data store 910 may illustratively be any non-transitory computer-readable data store, and in various embodiments may store any or all of the elements that are depicted in FIG. 9 as being loaded into a memory 920.

The processor 902 may also communicate to and from the memory 920. The memory 920 may contain computer program instructions (grouped as modules or components in some embodiments) that the processor 902 may execute in order to implement one or more embodiments. The memory 920 generally includes RAM, ROM, and/or other persistent, auxiliary, or non-transitory computer-readable media. The memory 920 may store an operating system 922 that provides computer program instructions for use by the processor 902 in the general administration and operation of the automatic incubator system 100. The memory 920 may further store specific computer-executable instructions and other information (which may be referred to herein as "modules" or "engines") for implementing aspects of the present disclosure. For example, the memory 920 may include the feature engine 926 and the machine learning model 928, which may be utilized by the intelligent manipulator subsystem 104 to implement aspects of the present disclosure as described above. The memory 920 may further store, for example, user interface module 924 that may enable presentation of information to the user interface 800 of FIG. 8. All of the modules or elements loaded into the memory 920 may also be stored in the data store 910 as various operations are performed.

It will be recognized that many of the components described in FIG. 9 are optional and that embodiments of the automatic incubator system 100 may or may not combine components. Furthermore, components need not be distinct or discrete. Components may also be reorganized, combined, and/or integrated. For example, the air analyzers 310A-310N in FIG. 3A may be combined and integrated together to conserve hardware resources (e.g., pressure sensor 312, composition sensor 314, temperature sensor 316, and/or humidity sensor 318). In some embodiments, components illustrated as part of the automatic incubator system 100 may additionally or alternatively be included in other computing devices, such that some aspects of the present disclosure may be performed by the automatic incubator system 100 while other aspects are performed by another computing device.

All of the methods and tasks described herein may be performed and fully automated by a computer system. The computer system may, in some cases, include multiple distinct computers or computing devices (e.g., physical servers, workstations, storage arrays, cloud computing resources, etc.) that communicate and interoperate over a network to perform the described functions. Each such computing device typically includes a processor (or multiple processors) that executes program instructions or modules stored in a memory or other non-transitory computer-readable storage medium or media or device (e.g., solid state storage devices, disk drives, etc.). The various functions disclosed herein may be embodied in such program instructions, or may be implemented in application-specific circuitry (e.g., ASICs or FPGAs) of the computer system. Where the computer system includes multiple computing devices, these devices may, but need not, be co-located. The results of the disclosed methods and tasks may be persistently stored by transforming physical storage devices, such as solid-state memory chips or magnetic disks, into a different state. In some embodiments, the computer system may be a cloud-based computing system whose processing resources are shared by multiple distinct business entities or other users.

The processes described herein or illustrated in the figures of the present disclosure may begin in response to an event, such as on a predetermined or dynamically determined schedule, on demand when initiated by a user or system administrator, or in response to some other event. When such processes are initiated, a set of executable program instructions stored on one or more non-transitory computer-readable media (e.g., hard drive, flash memory, removable media, etc.) may be loaded into memory (e.g., RAM) of a server or other computing device. The executable instructions may then be executed by a hardware-based computer processor of the computing device. In some embodiments, such processes or portions thereof may be implemented on multiple computing devices and/or multiple processors, serially or in parallel.

Depending on the embodiment, certain acts, events, or functions of any of the processes or algorithms described herein can be performed in a different sequence, can be added, merged, or left out altogether (e.g., not all described operations or events are necessary for the practice of the algorithm). Moreover, in certain embodiments, operations or events can be performed concurrently, e.g., through multi-threaded processing, interrupt processing, or multiple processors or processor cores or on other parallel architectures, rather than sequentially.

The various illustrative logical blocks, modules, routines, and algorithm steps described in connection with the embodiments disclosed herein can be implemented as electronic hardware (e.g., ASICs or FPGA devices), computer software that runs on computer hardware, or combinations of both. Moreover, the various illustrative logical blocks and modules described in connection with the embodiments disclosed herein can be implemented or performed by a machine, such as a processor device, a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. A processor device can be a microprocessor, but in the alternative, the processor device can be a controller, microcontroller, or state machine, combinations of the same, or the like. A processor device can include electrical circuitry configured to process computer-executable instructions. In another embodiment, a processor device includes an FPGA or other programmable device that performs logic operations without processing computer-executable instructions. A processor device can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor device may also include primarily analog components. For example, some or all of the rendering techniques described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, routine, or algorithm described in connection with the embodiments disclosed herein can be embodied directly in hardware, in a software module executed by a processor device, or in a combination of the two. A software module can reside in RAM memory, flash memory, ROM memory, EPROM memory, EEPROM memory, registers, hard disk, a removable disk, a CD-ROM, or any other form of a non-transitory computer-readable storage medium. An exemplary storage medium can be coupled to the processor device such that the processor device can read information from, and write information to, the storage medium. In the alternative, the storage medium can be integral to the processor device. The processor device and the storage medium can reside in an ASIC. The ASIC can reside in a user terminal. In the alternative, the processor device and the storage medium can reside as discrete components in a user terminal.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements or steps. Thus, such conditional language is not generally intended to imply that features, elements or steps are in any way required for one or more embodiments or that one or more embodiments necessarily include logic for deciding, with or without other input or prompting, whether these features, elements or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, or Z). Thus, such disjunctive language is not generally intended to, and should not, imply that certain embodiments require at least one of X, at least one of Y, and at least one of Z to each be present.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A system for cell culture within a case that structurally accommodates at least a first chamber, a second chamber, and at least a portion of an environment control subsystem, the system comprising:
   the first chamber configured to store a plurality of culture vessels including biological samples;
   the second chamber adjacent to the first chamber and fluidically isolated from the first chamber by first one or more movable structures based on the first one or more movable structures being in a closed configuration, wherein the second chamber is configured to accommodate at least a manipulator assembly for manipulating the plurality of culture vessels; and
   the environment control subsystem, wherein the environment control subsystem individually controls respective environments within the first chamber and the second chamber, and wherein the environment control subsystem is configured to:
      detect a first environment condition that specifies a current temperature of the first chamber, a current humidity of the first chamber, and a current air composition of the first chamber;
      detect a second environment condition that specifies a current temperature of the second chamber, a current humidity of the second chamber, and a current air composition of the second chamber;
      supply, via a first airflow mode determined based on a first cell culture activity conducted inside the first chamber, a first airflow to the first chamber to adjust the first environment condition toward a first target environment condition; and
      supply, via a second airflow mode determined based on a second cell culture activity conducted inside the second chamber, a second airflow to the second chamber to adjust the second environment condition toward a second target environment condition.

2. The system of claim 1, wherein the environment control subsystem comprises a housing that houses at least a portion of an air quality controller, wherein the housing is outside the case, and wherein the air quality controller is configured to supply the first airflow and the second airflow.

3. The system of claim 2, wherein the air quality controller comprises an air heater, a humidifier, a volatile organic compounds (VOC) filter, a high-efficiency particulate air (HEPA) filter, an oxygen absorber, and a carbon dioxide absorber.

4. The system of claim 3, wherein the environment control subsystem comprises a first airflow assembly and a second airflow assembly, and wherein:
   the first airflow assembly supplies the first airflow to the first chamber to adjust the first environment condition toward the first target environment condition; and
   the second airflow assembly supplies the second airflow to the second chamber to adjust the second environment condition toward the second target environment condition.

5. The system of claim 4, wherein a first end of the first airflow assembly is inside the housing and a second end of the first airflow assembly is inside the first chamber, and wherein a first end of the second airflow assembly is inside the housing and a second end of the second airflow assembly is inside the second chamber.

6. The system of claim 5, wherein the environment control subsystem comprises a plurality of sensors configured to detect the first environment condition and the second environment condition, and wherein the plurality of sensors are housed in the housing and comprise a pressure sensor, a temperature sensor, a humidity sensor, and an air composition sensor.

7. The system of claim 1, wherein when the first airflow mode is a one-way airflow mode, to supply the first airflow comprises injecting air inlets from an air tank without circulating air inside the first chamber.

8. The system of claim 7, wherein the environment control subsystem comprises an air reservoir that is different from the air tank, and wherein the environment control subsystem is further configured to:
   determine that the current air composition of the first chamber deviates from an air composition specified by the first target environment condition above a predetermined threshold; and
   responsive to determining that the current air composition of the first chamber deviates from the air composition specified by the first target environment condition, cause the air reservoir to flush air to the first chamber to adjust the current air composition of the first chamber toward the air composition specified by the first target environment condition.

9. The system of claim 1, wherein when the first airflow mode is a close airflow mode, to supply the first airflow comprises circulating air inside the first chamber without injecting air inlets from an air tank.

10. The system of claim 1, wherein when the first airflow mode is a semi-close airflow mode, to supply the first airflow comprises circulating air inside the first chamber and injecting air inlets from an air tank according to a predetermined ratio.

11. The system of claim 1, wherein the first airflow mode is a one-way airflow mode, and the second airflow mode is a semi-close airflow mode or a close airflow mode.

12. The system of claim 1, wherein the first cell culture activity conducted inside the first chamber comprises culturing unknown cells or cells that are toxic to an environment external to the case.

13. The system of claim 1, wherein the environment control subsystem comprises a first heater deployed inside the first chamber, and wherein the environment control subsystem is further configured to activate the first heater to adjust the current temperature of the first chamber toward a temperature specified by the first target environment condition.

14. The system of claim 1, wherein the environment control subsystem comprises a first air absorber deployed outside the first chamber, and wherein the environment control subsystem activates the first air absorber based on the first airflow mode to adjust the current air composition of the first chamber toward an air composition specified by the first target environment condition.

15. The system of claim 1, wherein a temperature specified by the first target environment condition is between 36.5° C. (Celsius) to 37.5° C., a humidity specified by the first target environment condition is between 38% to 42%, and an air composition specified by the first target environment condition comprises 5%-7% oxygen, 5%-10% carbon dioxide, and 88%-90% nitrogen.

16. The system of claim 1, wherein a combined volume of the first chamber and the second chamber is less than 500 L.

17. The system of claim 1, wherein to supply the first airflow comprises filtering air inlets from an air tank and/or air inside the first chamber using a volatile organic compounds (VOC) filter and a high-efficiency particulate air (HEPA) filter.

18. The system of claim 1, wherein the environment control subsystem is further configured to determine the first airflow mode based at least on a size of the first chamber or a remaining capacity of an air tank that supplies the first airflow.

19. The system of claim 1, wherein the environment control subsystem is further configured to determine the second airflow mode based at least on a size of the second chamber or a remaining capacity of an air tank that supplies the second airflow.

20. The system of claim 1, wherein:
when the first airflow mode is a one-way airflow mode, the environment control subsystem is further configured to control a total air change per hour (TACH) associated with the first chamber without controlling a fresh air change per hour (FACH) associated with the first chamber; and
when the first airflow mode is a semi-close airflow mode or a close airflow mode, the environment control subsystem is further configured to control the TACH associated with the first chamber and the FACH associated with the first chamber.

21. The system of claim 1, further comprising an intelligent manipulator subsystem that comprises the manipulator assembly, a camera assembly, a thermal camera, one or more processors and non-transitory computer storage media storing instructions, wherein:
the camera assembly is configured to generate image data;
the thermal camera is configured to generate thermal imaging data; and
the one or more processors are configured to execute the instructions to generate, via a machine learning model based on the image data and the thermal imaging data, one or more thermal control signals,
wherein the environment control subsystem supplies the first airflow and the second airflow further based on the one or more thermal control signals.

22. The system of claim 21, wherein the environment control subsystem supplies the first airflow and the second airflow further based on the one or more thermal control signals.

23. The system of claim 21, wherein the machine learning model is configured to: extract features associated with one or more objects to be manipulated by the manipulator assembly based on the image data and/or the thermal imaging data, and generate real-time information associated with the one or more objects based on the features.

24. The system of claim 1, further comprising a third chamber configured to conduct a cryopreservation procedure or a thawing procedure, wherein the third chamber is adjacent to the second chamber and fluidically isolated from the second chamber by second one or more movable structures based on the second one or more movable structures being in the closed configuration, and wherein the environment control subsystem is further configured to:
detect a third environment condition that specifies a current temperature of the third chamber, a current humidity of the third chamber, and a current air composition of the third chamber; and
supply, via a third airflow mode determined based on a third cell culture activity conducted inside the third chamber, a third airflow to the third chamber to adjust the third environment condition toward a third target environment condition.

25. A method implemented by a miniaturized system for cell culture, wherein the miniaturized system comprises a first chamber configured to store a plurality of culture vessels including biological samples and a second chamber configured to accommodate at least a manipulator assembly for manipulating the plurality of culture vessels, the method comprising:
detecting a first environment condition that specifies a current temperature of the first chamber, a current humidity of the first chamber, and a current air composition of the first chamber;
detecting a second environment condition that specifies a current temperature of the second chamber, a current humidity of the second chamber, and a current air composition of the second chamber;
supplying, via a first airflow mode determined based on a first cell culture activity conducted inside the first chamber, a first airflow to the first chamber to adjust the first environment condition toward a first target environment condition; and
supplying, via a second airflow mode determined based on a second cell culture activity conducted inside the second chamber, a second airflow to the second chamber to adjust the second environment condition toward a second target environment condition.

26. The method of claim 25, wherein when the first airflow mode is a one-way airflow mode, supplying the first airflow comprises injecting air inlets from an air tank without circulating air inside the first chamber.

27. The system of claim 1, wherein the second cell culture activity comprises manipulating oocytes, embryos, ovums, or sperms.

28. A system for cell culture within a case that structurally accommodates at least a first chamber, a second chamber, and at least a portion of an environment control subsystem, the system comprising:
the first chamber configured to store a plurality of culture vessels including biological samples;
the second chamber adjacent to the first chamber and fluidically isolated from the first chamber by first one or more movable structures based on the first one or more movable structures being in a closed configuration, wherein the second chamber is configured to accommodate at least a manipulator assembly for manipulating the plurality of culture vessels; and
the environment control subsystem configured to:
detect a first environment condition that specifies a current temperature of the first chamber, a current humidity of the first chamber, and a current air composition of the first chamber;
detect a second environment condition that specifies a current temperature of the second chamber, a current humidity of the second chamber, and a current air composition of the second chamber;
supply, via a first airflow mode, a first airflow to the first chamber to adjust the first environment condition toward a first target environment condition; and supply, via a second airflow mode, a second airflow to the second chamber to adjust the second environment condition toward a second target environment condition, wherein:
when the first airflow mode is a one-way airflow mode, to supply the first airflow comprises injecting air inlets from an air tank without circulating air inside the first chamber;

when the first airflow mode is a close airflow mode, to supply the first airflow comprises circulating the air inside the first chamber without injecting the air inlets from the air tank; and when the first airflow mode is a semi-close airflow mode, to supply the first airflow comprises circulating the air inside the first chamber and injecting the air inlets from the air tank according to a predetermined ratio.

29. The system of claim 28, wherein the environment control subsystem is further configured to:
determine the first airflow mode based on a first cell culture activity conducted inside the first chamber; and
determine the second airflow mode based on a second cell culture activity conducted inside the second chamber.

30. The system of claim 29, wherein the first cell culture activity comprises culturing unknown cells or cells that are toxic to an environment external to the case.

31. The system of claim 29, wherein the second cell culture activity comprises manipulating oocytes, embryos, ovums, or sperms.

32. The method of claim 25, wherein the second cell culture activity comprises manipulating oocytes, embryos, ovums, or sperms.

* * * * *